(12) United States Patent
Wieja et al.

(10) Patent No.: US 10,118,906 B2
(45) Date of Patent: Nov. 6, 2018

(54) USE OF SUBSTITUTED OXADIAZOLES FOR COMBATING PHYTOPATHOGENIC FUNGI

(71) Applicant: BASF SE, Ludwigshafen (DE)

(72) Inventors: Andy Wieja, Ludwigshafen (DE); Christian Winter, Ludwigshafen (DE); Claudia Rosenbaum, Einhausen (DE); Doris Kremzow-Graw, Heidelberg (DE); Franz Roehl, Goennheim (DE); Joachim Rheinheimer, Ludwigshafen (DE); Manojkumar Poonoth, Mannheim (DE); Violeta Terteryan, Mannheim (DE); Egon Haden, Speyer (DE); Ana Escribano Cuesta, Mannheim (DE); Janosch Harald Achenbach, Frankfurt (DE); Tobias Mentzel, Roemerberg (DE); Christine Wiebe, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/316,399

(22) PCT Filed: Jun. 1, 2015

(86) PCT No.: PCT/EP2015/062100
§ 371 (c)(1),
(2) Date: Dec. 5, 2016

(87) PCT Pub. No.: WO2015/185485
PCT Pub. Date: Dec. 10, 2015

(65) Prior Publication Data
US 2017/0144980 A1  May 25, 2017

(30) Foreign Application Priority Data
Jun. 6, 2014 (EP) .................................... 14171528

(51) Int. Cl.
| | | |
|---|---|---|
| A01N 43/82 | (2006.01) |
| C07D 271/06 | (2006.01) |
| A01N 43/90 | (2006.01) |
| C07D 413/04 | (2006.01) |
| C07D 413/10 | (2006.01) |
| C07D 413/12 | (2006.01) |
| C07D 417/12 | (2006.01) |
| C07D 487/04 | (2006.01) |
| C07D 495/04 | (2006.01) |

(52) U.S. Cl.
CPC .......... *C07D 271/06* (2013.01); *A01N 43/82* (2013.01); *A01N 43/90* (2013.01); *C07D 413/04* (2013.01); *C07D 413/10* (2013.01); *C07D 413/12* (2013.01); *C07D 417/12* (2013.01); *C07D 487/04* (2013.01); *C07D 495/04* (2013.01)

(58) Field of Classification Search
CPC ........................................................ A01N 43/82
USPC ......................................................... 514/364
See application file for complete search history.

(56) References Cited

U.S. PATENT DOCUMENTS 4,871,753 A * 10/1989 Rohr ...................... A01N 43/82
514/364

FOREIGN PATENT DOCUMENTS

| DE | 195 36 811 | 4/1997 |
|---|---|---|
| EP | 0 393 936 | 10/1990 |
| JP | 2001 316378 | 11/2001 |
| WO | WO-2011/088181 | 7/2011 |
| WO | WO-2011/088192 | 7/2011 |
| WO | WO-2012/100342 | 8/2012 |
| WO | WO-2013/006408 | 1/2013 |
| WO | WO-2013/008162 | 1/2013 |
| WO | WO-2013/017657 | 2/2013 |
| WO | WO-2013/080120 | 6/2013 |
| WO | WO-2014/062549 | 4/2014 |

OTHER PUBLICATIONS

Andrianov et al., "Rearrangements of 1-oxa-2-azoles. 4. Synthesis and Rearrangement of Amidoximes of Isoxazole- and 4,5-Dihydroisoxazole-3-Carboxylic Acids," CAS Accession No. 1992:6493.

(Continued)

*Primary Examiner* — Kevin E Weddington
(74) *Attorney, Agent, or Firm* — Brinks Gilson & Lione

(57) ABSTRACT

The present invention relates to the use of novel oxadiazoles of the formula I or an N-oxide and/or their agriculturally useful salts for controlling phytopathogenic fungi, or to a method for combating phytopathogenic harmful fungi, which process comprises treating the fungi or the materials, plants, the soil or seeds to be protected against fungal attack, with an effective amount of at least one compound of formula I or an N-oxide or an agriculturally acceptable salt thereof; and to agrochemical compositions comprising at least one such compound and to agrochemical compositions further comprising seeds.

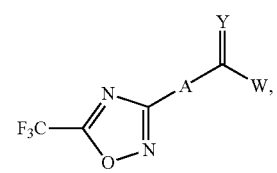

16 Claims, No Drawings

(56) References Cited

OTHER PUBLICATIONS

Goddard, "5-Heteroaryl-2-Thiophenecarboxylic Acids: Oxazoles and Oxadiazoles," *Journal of Heterocyclic Chemistry*, 1991, vol. 28, No. 17, pp. 17-28, CAS Accession No. 1991:185346.
Hemming, "Product Class 6: 1,2,4-Oxadiazoles," *Science of Synthesis*, pp. 127-184, CAS Accession No. 2004:204619.
Liu et al., "Design, Synthesis, and Biological Evaluation of N-Carboxyphenylpyrrole Derivatives as Potent HIV Fusion Inhibitors Targeting gp41," CAS Accession No. 2008:1411348.
Tale et al., "Synthesis and Antibacterial, Antifungal Activity of Novel 1,2,4-Oxadiazole," *Journal of Chemical and Pharmaceutical Research*, 2011, vol. 3, No. 2, pp. 496-505, CAS Accession No. 2011:495843.
European Search Report dated Jan. 7, 2015 for EP Application No. 14171528.4.
International Search Report dated Sep. 17, 2015 for PCT/EP2015/062100.

\* cited by examiner

USE OF SUBSTITUTED OXADIAZOLES FOR COMBATING PHYTOPATHOGENIC FUNGI

This application is a National Stage application of International Application No. PCT/EP2015/062100, filed Jun. 1, 2015. This application also claims priority under 35 U.S.C. § 119 to European Patent Application No. 14171528.4, filed Jun. 6, 2014.

The present invention relates to the use of novel oxadiazoles of the formula I or an N-oxide and/or their agriculturally useful salts for controlling phytopathogenic fungi, or to a method for combating phytopathogenic harmful fungi, which process comprises treating the fungi or the materials, plants, the soil or seeds to be protected against fungal attack, with an effective amount of at least one compound of formula I or an N-oxide or an agriculturally acceptable salt thereof; and to agrochemical compositions comprising at least one such compound and to agrochemical compositions further comprising seeds.

EP 276432 A2 relates to similar 3-phenyl-5-trifluoromethyl-oxadiazole derivatives and to their use to combat phytopathogenic microorganisms. WO 2013/008162 A1 and WO 2013/080120 A1 relate to novel trifluoromethyl-oxadiazole derivatives and their use as medicaments, particularly for the treatment of neurodegeneration, muscle atrophy or diabetes/metabolic syndrome via inhibition of histone deacetylase HDAC4.

In many cases, in particular at low application rates, the fungicidal activity of known fungicidal compounds is unsatisfactory. Based on this, it was an object of the present invention to provide compounds having improved activity and/or a broader activity spectrum against phytopathogenic fungi. This objective is achieved by the use of oxadiazoles of the formula I and/or their agriculturally useful salts for controlling phytopathogenic fungi.

The compounds according to the invention differ from those described in EP 276432 A2 in the nature of the group —(C=Y)—W— on ring A.

Accordingly, the present invention relates to the use of compounds of the formula I

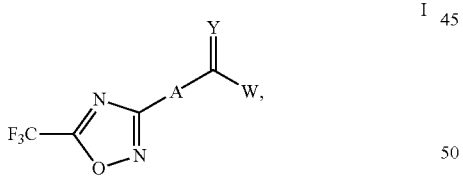

wherein:
A is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^A$; wherein
  $R^A$ is halogen, cyano, $NO_2$, OH, SH, $NH_2$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and alicyclic moieties are unsubstituted or substituted by 1, 2, 3 or 4 identical or different groups $R^a$; wherein
    $R^a$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl, $C_1$-$C_4$-alkoxy-$C_1$-$C_4$-alkyl;
Y is O or S;
W is $NR^1R^2$ or $OR^3$; wherein
  $R^1$, $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)—($C_1$-$C_6$-alkyl), C(=O)—($C_1$-$C_6$-alkoxy), phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$;
  or $R^1$ and $R^2$ together with the nitrogen atom to which they are bound form a saturated or partially unsaturated mono- or bicyclic 3- to 10-membered heterocycle, wherein the heterocycle includes beside one nitrogen atom and one or more carbon atoms 1, 2 or 3 heteroatoms independently selected from N, O and S as ring member atoms; and wherein one or two $CH_2$ groups of the heterocycle may be replaced by one or two groups independently selected from the group of C(=O) and C(=S); and wherein the heterocycle is unsubstituted or carries 1, 2, 3, 4 or up to the maximum possible number of identical or different groups $R^{1a}$; wherein
    $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $NHSO_2$—$C_1$-$C_4$-alkyl, (C=O) $C_1$-$C_4$-alkyl, C(=O)—$C_1$-$C_4$-alkoxy, $C_1$-$C_6$-alkylsulfonyl, hydroxy$C_1$-$C_4$-alkyl, C(=O)—$NH_2$, C(=O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl or $C_1$-$C_4$-alkoxy-$C_1$-$C_4$-alkyl;
  $R^3$ is $C_2$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, phenyl-$C_1$-$C_4$-alkyl or heteroaryl-$C_1$-$C_4$-alkyl; wherein the heteroaryl group is a 5- or 6-membered aromatic heterocycle, wherein the ring member atoms of the heterocyclic ring include besides carbon atoms 1, 2, 3 or 4 heteroatoms selected from N, O and S as ring member atoms and wherein the cyclic groups are unsubstituted or substituted by 1, 2, 3 or up to the maximum possible number of identical or different groups $R^{3a}$;
  or phenyl, naphthyl or a 3- to 10-membered saturated, partially unsaturated or aromatic mono- or bicyclic heterocycle, wherein the ring member atoms of the heterocycle include besides carbon atoms 1, 2, 3 or 4 heteroatoms selected from N, O and S as ring member atoms; and wherein 1 or 2 carbon ring member atoms of the heterocycle may be replaced by 1 or 2 groups independently selected from C(=O) and C(=S); and wherein the aliphatic or cyclic groups $R^3$ are unsubstituted or substituted by 1, 2, 3 or up to the maximum possible number of identical or different groups $R^{3a}$; wherein $R^{3a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl, hydroxy$C_1$-$C_4$-alkyl, C(=O)—$NH_2$, C(=O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl or $C_1$-$C_4$-alkoxy-$C_1$-$C_4$-alkyl;

or the N-oxides or the agriculturally acceptable salts thereof for combating phytopathogenic harmful fungi.

Agriculturally useful salts of the compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound I with an acid of the corresponding anion, preferably of hydrochloric acid, hydrobromic acid, sulfuric acid, phosphoric acid or nitric acid.

Compounds I can exist as one or more stereoisomers. The various stereoisomers include enantiomers, diastereomers, atropisomers arising from restricted rotation about a single bond of asymmetric groups and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers.

The compounds of the invention may be present as a mixture of stereoisomers, e.g. a racemate, individual stereoisomers, or as an optically active form.

Compounds of formula I can be present in different crystal modifications whose biological activity may differ. They also form part of the subject matter of the present invention. The compounds of formula I can be present in atropisomers arising from restricted rotation about a single bond of asymmetric groups. They also form part of the subject matter of the present invention.

In respect of the variables, the embodiments of the intermediates obtained during preparation of compounds I correspond to the embodiments of the compounds of formula I. The term "compounds I" refers to compounds of formula I.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromo¬ethoxy, 4-fluorobutoxy, 4-chlorobutoxy, 4-bromobutoxy or nonafluorobutoxy.

The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or hetereoaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_6$-alkylsulfinyl" refers to straight-chain or branched alkyl groups having 1 to 6 carbon atoms (as defined above) bonded through a —S(=O)— moiety, at any position in the alkyl group, for example methylsulfinyl and ethylsulfinyl, and the like. Accordingly, the term "$C_1$-$C_6$-haloalkylsulfinyl" refers to straight-chain or branched haloalkyl group having 1 to 6 carbon atoms (as defined above), bonded through a —S(=O)— moiety, at any position in the haloalkyl group.

The term "$C_1$-$C_6$-alkylsulfonyl" refers to straight-chain or branched alkyl groups having 1 to 6 carbon atoms (as defined above), bonded through a —S(=O)$_2$— moiety, at any position in the alkyl group, for example methylsulfonyl. Accordingly, the term "$C_1$-$C_6$-haloalkylsulfonyl" refers to straight-chain or branched haloalkyl group having 1 to 6 carbon atoms (as defined above), bonded through a —S(=O)$_2$— moiety, at any position in the haloalkyl group.

The term "hydroxy$C_1$-$C_4$-alkyl" refers to alkyl having 1 to 4 carbon atoms, wherein one hydrogen atom of the alkyl radical is replaced by a OH group.

The term "amino$C_1$-$C_4$-alkyl" refers to alkyl having 1 to 4 carbon atoms, wherein one hydrogen atom of the alkyl radical is replaced by a NH$_2$ group.

The term "$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $C_1$-$C_4$-alkyl-NH— group which is bound through the nitrogen. Likewise the term "di$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a ($C_1$-$C_4$-alkyl)$_2$N— group which is bound through the nitrogen.

The term "aminocarbonyl-$C_1$-$C_4$-alkyl" refers to alkyl having 1 to 4 carbon atoms, wherein one hydrogen atom of the alkyl radical is replaced by a —(C=O)—NH$_2$ group.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_3$-$C_8$-cycloalkyl" refers to monocyclic saturated hydrocarbon radicals having 3 to 8 carbon ring members such as cyclopropyl ($C_3H_5$), cyclobutyl, cyclopentyl, cyclohexyl, cycloheptyl or cyclooctyl.

The term "$C_3$-$C_8$-cycloalkyl-$C_1$-$C_4$-alkyl" refers to a cycloalkyl radical having 3 to 8 carbon atoms (as defined above), which is bonded via a $C_1$-$C_4$-alkyl group as defined above.

The term "$C_3$-$C_8$-cycloalkyloxy" refers to a cycloalkyl radical having 3 to 8 carbon atoms (as defined above), which is bonded via an oxygen.

The term "C(=O)—($C_1$-$C_4$-alkyl)" refers to a radical which is attached through the carbon atom of the C(=O) group as indicated by the number valence of the carbon atom.

The term "$C_1$-$C_6$-alkoxyimino-$C_1$-$C_4$-alkyl" refers to a radical which is attached through a carbon atom of the $C_1$-$C_4$-alkyl chain, wherein one —CH$_2$— group is replaced by a —C(=N—O—($C_1$-$C_6$-alkoxy))-group. Likewise the terms $C_2$-$C_6$-alkenyloxyimino-$C_1$-$C_4$-alkyl and $C_3$-$C_6$-alkynyloxyimino-$C_1$-$C_4$-alkyl are to be construed.

The term "and wherein any of the aliphatic or cyclic groups are unsubstituted or substituted by 1, 2, 3 or up to the maximum possible number of identical or different groups $R^{1a}$" refers to aliphatic groups, cyclic groups and groups, which contain an aliphatic and a cyclic moiety in one group, such as in, for example, phenyl-$C_1$-$C_4$-alkyl; therefore a group which contains an aliphatic and a cyclic moiety both of these moieties may be substituted or unsubstituted independently of each other.

The term "saturated or partially unsaturated 3-, 4-5-, 6- or 7-membered carbocycle" is to be understood as meaning both saturated or partially unsaturated carbocycles having 3, 4, 5, 6 or 7 ring members. Examples include cyclopropyl, cyclopentyl, cyclopentenyl, cyclopentadienyl, cyclohexyl, cyclohexenyl, cyclohexadienyl, cycloheptyl, cycloheptenyl, cycloheptadienyl, and the like.

The term "saturated or partially unsaturated 3-, 4-, 5-, 6-, or 7-membered heterocycle, wherein the ring member atoms of the heterocycle include besides carbon atoms 1, 2, 3 or 4 heteroatoms independently selected from the group of N, O and S", is to be understood as meaning both saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4- dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding—ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding—ylidene radicals; and The term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

In respect of the variables, the embodiments of the intermediates correspond to the embodiments of the compounds I.

Preference is given to those compounds I and, where applicable, also to compounds of all sub-formulae provided herein, e.g. formulae I.a1 to I.a8 and I.b1 to I.b5.

Variables such as $R^1$, $R^2$, $R^3$, A, $R^4$, $R^a$, $R^{1a}$, Y, W, n have independently of each other or more preferably in combination (any possible combination of 2 or more substituents as defined herein) the following meanings:

In one embodiment of the invention A is phenyl which is unsubstituted or substituted by 1, 2, 3 or 4 identical or different groups $R^4$ as defined or preferably defined herein.

In another aspect of the invention A is phenyl which is unsubstituted or substituted by 1, 2, 3 or 4 identical or different groups $R^4$ as defined or preferably defined herein and wherein the group Y=C—W is attached to the phenyl ring in para-position with regard to the oxadiazole group.

In one aspect of the invention A is phenyl which is unsubstituted or substituted by 1, 2, 3 or 4 identical or different groups $R^4$ as defined or preferably defined herein and wherein the group Y=C—W is attached to the phenyl ring in meta-position with regard to the oxadiazole group.

In another embodiment A is a 6-membered aromatic heterocycle, wherein the ring member atoms of the heterocyclic ring include besides carbon atoms 1 or 2 nitrogen atoms as ring member atoms; and wherein the cyclic groups A are unsubstituted or substituted by 1, 2 or 3 identical or different groups $R^4$ as defined or preferably defined herein.

In a further embodiment A is a 6-membered aromatic heterocycle, wherein the ring member atoms of the heterocyclic ring include besides carbon atoms 1 or 2 nitrogen atoms as ring member atoms; and wherein the cyclic groups A are unsubstituted or substituted by 1, 2 or 3 identical or different groups $R^4$ as defined or preferably defined herein and wherein the group Y=C—W is attached to the 6-membered aromatic heterocycle in para-position with regard to the oxadiazole group.

In another embodiment A is a 6-membered aromatic heterocycle, wherein the ring member atoms of the heterocyclic ring include besides carbon atoms 1 or 2 nitrogen atoms as ring member atoms; and wherein the cyclic groups A are unsubstituted or substituted by 1, 2 or 3 identical or different groups $R^4$ as defined or preferably defined herein and wherein the group Y=C—W is attached to the 6-membered aromatic heterocycle in meta-position with regard to the oxadiazole group.

In still another embodiment A is a pyridine ring which is unsubstituted or substituted by 1, 2 or 3 identical or different groups $R^4$ as defined or preferably defined herein and wherein the group Y=C—W is attached to the pyridine ring in para-position with regard to the oxadiazole group.

In one further aspect A is a pyridine ring which is unsubstituted or substituted by 1, 2 or 3 identical or different groups $R^4$ as defined or preferably defined herein and wherein the group Y=C—W is attached to the pyridine ring in meta-position with regard to the oxadiazole group.

In a further preferred embodiment A is a 5-membered aromatic heterocycle, wherein the ring member atoms of the heterocycle include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^4$ as defined or preferably defined herein.

In a further embodiment A is a thienyl, pyrazolyl, oxazolyl, isoxazolyl, thiazolyl or isothiazolyl; and wherein the cyclic groups A are unsubstituted or substituted by 1, 2, 3 or 4 identical or different groups $R^4$ as defined or preferably defined herein.

In still a further embodiment A is a thienyl, pyrazolyl, oxazolyl, isoxazolyl, thiazolyl or isothiazolyl; wherein the oxadiazol ring and the group Y=C—W are attached to the thienyl ring in 2,5-position or the oxadiazol ring and the group Y=C—W are attached to the pyrazolyl, isothiazolyl, isoxazolyl ring in 3,5-position or the oxadiazol ring and the group Y=C—W are attached to the thiazolyl or oxazolyl, ring in 2,4- or 2,5-position; and wherein the cyclic groups A are unsubstituted or substituted by 1, 2, 3 or 4 identical or different groups $R^4$ as defined or preferably defined herein.

In one embodiment A is thienyl; wherein the oxadiazol ring and the group Y═C—W are attached to the thienyl ring in 2,5-position; and wherein the thienyl is unsubstituted or substituted by 1, 2, 3 or 4 identical or different groups $R^A$ as defined or preferably defined herein.

In one embodiment A is thienyl; wherein the oxadiazol ring and the group Y═C—W are attached to the thienyl ring in 3,5-position or 5,3-position; and wherein the thienyl is unsubstituted or substituted by 1, 2, 3 or 4 identical or different groups $R^A$ as defined or preferably defined herein.

In a preferred embodiment of the invention $R^A$ is halogen, cyano, $C_1$-$C_6$-alkyl, $C_1$-$C_6$-alkoxy, $C_2$-$C_6$-alkenyl, $C_2$-$C_6$-alkynyl or $C_3$-$C_8$-cycloalkyl; and wherein the aliphatic and alicyclic moieties are unsubstituted or substituted by 1, 2, 3 or 4 identical or different groups $R^a$ as defined or preferably defined herein. In another preferred embodiment of the invention $R^A$ is halogen, cyano, $C_1$-$C_6$-alkyl, $C_1$-$C_6$-alkoxy, $C_2$-$C_6$-alkenyl, $C_2$-$C_6$-alkynyl or $C_3$-$C_8$-cycloalkyl; and wherein the aliphatic and alicyclic moieties are unsubstituted or substituted by 1, 2, 3 or 4 identical or different groups selected from halogen, cyano, $C_1$-$C_6$-alkyl, $C_1$-$C_6$-alkoxy and $C_3$-$C_8$-cycloalkyl, in particular fluorine.

More preferably $R^A$ is halogen, cyano, $C_1$-$C_6$-alkyl, $C_1$-$C_6$-haloalkyl, $C_1$-$C_6$-alkoxy or $C_1$-$C_6$-haloalkoxy; in particular halogen, $C_1$-$C_6$-alkyl or $C_1$-$C_6$-haloalkyl; more particularly chlorine, fluorine, methyl, trifluoromethyl, difluoromethyl or fluoromethyl. Even more particularly chlorine, fluorine or methyl.

$R^a$ according to the invention is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl. In a preferred embodiment of the invention $R^a$ is halogen, cyano, $C_1$-$C_6$-alkyl, $C_1$-$C_6$-alkoxy or $C_3$-$C_8$-cycloalkyl. More preferably $R^a$ is halogen, in particular fluorine.

Y according to the invention is O or S. In a preferred embodiment Y is O.

In one aspect of the invention W is $NR^1R^2$, wherein $R^1$ and $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(═O)—($C_1$-$C_6$-alkyl) or C(═O)—($C_1$-$C_6$-alkoxy); and wherein any of the above-mentioned aliphatic or cyclic groups are unsubstituted or substituted by 1, 2, 3 or up to the maximum possible number of identical or different groups $R^{1a}$ as defined or preferably defined herein.

In one aspect of the invention W is $NR^1R^2$, wherein $R^1$ and $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl; and wherein any of the above-mentioned aliphatic or cyclic groups are unsubstituted or substituted by 1, 2, 3 or up to the maximum possible number of identical or different groups $R^{1a}$ as defined or preferably defined herein.

In a further aspect of the invention W is $NR^1R^2$, wherein $R^1$ is hydrogen, $C_1$-$C_6$-alkyl, $C_2$-$C_6$-alkenyl or $C_2$-$C_6$-alkynyl and $R^2$ is phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle wherein the ring includes besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$ as defined or preferably defined herein.

In another aspect of the invention W is $NR^1R^2$, wherein $R^1$ and $R^2$ together with the nitrogen atom to which they are bound form a saturated or partially unsaturated 3- to 6-membered heterocycle, wherein the heterocycle includes beside one nitrogen atom and one or more carbon atoms 1, 2 or 3 heteroatoms independently selected from N, O and S as ring member atoms; and wherein one or two $CH_2$ groups of the heterocycle may be replaced by one or two groups independently selected from the group of C(═O) and C(═S); and wherein the heterocycle is unsubstituted or carries 1, 2, 3, 4 or up to the maximum possible number of identical or different groups $R^{1a}$ as defined or preferably defined herein.

In still another aspect of the invention W is $NR^1R^2$, wherein $R^1$ and $R^2$ together with the nitrogen atom to which they are bound form a saturated or partially unsaturated 3- to 6-membered heterocycle, wherein the heterocycle includes beside one nitrogen atom and one or more carbon atoms one additional heteroatom selected from N, O and S as ring a member atom; and wherein the heterocycle is unsubstituted or carries 1, 2, 3, 4 or up to the maximum possible number of identical or different groups $R^{1a}$ as defined or preferably defined herein.

In one embodiment W is $NR^1R^2$, wherein $R^1$ is hydrogen and $R^2$ is $C_3$-$C_6$-cycloalkyl, wherein the cycloalkyl group is unsubstituted or carries 1, 2, 3, 4 or up to the maximum possible number of identical or different groups $R^{1a}$ as defined or preferably defined herein.

In one embodiment W is $NR^1R^2$, wherein $R^1$ is hydrogen and $R^2$ $C_1$-$C_6$-alkyl, $C_2$-$C_6$-alkenyl or $C_2$-$C_6$-alkynyl, wherein the aliphatic groups are unsubstituted or carry 1, 2, 3, 4 or up to the maximum possible number of identical or different groups $R^{1a}$ as defined or preferably defined herein.

In one embodiment W is $NR^1R^2$, wherein $R^1$ is hydrogen and $R^2$ is heteroaryl-$C_1$-$C_4$-alkyl, wherein any of the aliphatic or cyclic groups are unsubstituted or substituted by 1, 2, 3 or up to the maximum possible number of identical or different groups $R^{1a}$ as defined or preferably defined herein.

In one embodiment W is $NR^1R^2$, wherein $R^1$ is hydrogen and $R^2$ is phenyl, wherein the phenyl group is unsubstituted or carries 1, 2, 3, 4 or up to the maximum possible number of identical or different groups $R^{1a}$ as defined or preferably defined herein.

In a preferred embodiment of the invention $R^{1a}$ is halogen, cyano, $C_1$-$C_6$-alkyl, $C_1$-$C_6$-haloalkyl, $C_1$-$C_6$-alkoxy, $C_1$-$C_6$-haloalkoxy or $C_3$-$C_8$-cycloalkyl.

In another preferred aspect of the invention $R^{1a}$ is halogen, cyano, $C_1$-$C_6$-alkyl, $C_1$-$C_6$-haloalkyl, $C_1$-$C_6$-alkoxy or $C_1$-$C_6$-haloalkoxy.

In a more preferred aspect of the invention $R^{1a}$ is halogen or cyano; in particular halogen; most particularly fluorine.

In a preferred embodiment of the invention $R^3$ is $C_2$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, phenyl-$C_1$-$C_4$-alkyl or heteroaryl-$C_1$-$C_4$-alkyl; and wherein the heteroaryl group is a 5- or 6-membered aromatic heterocycle, wherein the ring member atoms of the heterocyclic ring include besides carbon atoms 1, 2, 3 or 4 heteroatoms selected from N, O and S as ring member atoms and wherein the cyclic groups are unsubstituted or substituted by 1, 2 or 3 identical or different groups selected from halogen, cyano, $C_1$-$C_6$-alkyl, $C_1$-$C_6$-alkoxy and $C_3$-$C_8$-cycloalkyl.

In another preferred embodiment of the invention $R^3$ is $C_3$-$C_6$-cycloalkyl, $C_3$-$C_6$-cycloalkenyl, phenyl-$C_1$-$C_4$-alkyl or heteroaryl-$C_1$-$C_4$-alkyl; and wherein the heteroaryl group is a 5- or 6-membered aromatic heterocycle, wherein the ring member atoms of the heterocyclic ring include besides carbon atoms 1, 2, 3 or 4 heteroatoms selected from N, O and S as ring member atoms and wherein the cyclic groups are unsubstituted or substituted by 1, 2 or 3 identical or different groups selected from halogen, cyano, $C_1$-$C_6$-alkyl, $C_1$-$C_6$-alkoxy and $C_3$-$C_8$-cycloalkyl.

In another preferred embodiment of the invention $R^3$ is phenyl or a 5- to 6-membered aromatic heterocycle, wherein the ring member atoms of the heterocycle include besides carbon atoms 1, 2 or 3 heteroatoms selected from N, O and S as ring member atoms; and wherein the aliphatic or cyclic groups selected from halogen, cyano, $C_1$-$C_6$-alkyl, $C_1$-$C_6$-alkoxy and $C_3$-$C_8$-cycloalkyl.

In one preferred embodiment of the invention $R^{3a}$ is halogen, cyano, $NO_2$, $C_1$-$C_6$-alkyl, $C_1$-$C_6$-haloalkyl, $C_1$-$C_6$-alkoxy, $C_1$-$C_6$-haloalkoxy or $C_3$-$C_8$-cycloalkyl. In a further preferred embodiment of the invention $R^{3a}$ is halogen, $C_1$-$C_6$-alkyl, $C_1$-$C_6$-haloalkyl, $C_1$-$C_6$-alkoxy or $C_1$-$C_6$-haloalkoxy, in particular halogen, more particularly chlorine or fluorine.

In one further preferred embodiment the invention relates to the use of compounds (I.a1) of formula I, wherein:
A is phenyl, pyridyl or thienyl; and wherein the cyclic groups A are unsubstituted or substituted by 1, 2, 3 or 4 identical or different groups $R^A$; wherein
$R^A$ is halogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and alicyclic moieties are unsubstituted or substituted by 1, 2, 3 or 4 identical or different groups $R^a$; wherein
$R^a$ is halogen, cyano, $C_1$-$C_6$-alkyl, $C_1$-$C_6$-alkoxy or $C_3$-$C_8$-cycloalkyl;
n is 0, 1, 2 or 3;
Y is O;
W is $NR^1R^2$;
$R^1$ is hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)—($C_1$-$C_6$-alkyl) or C(=O)—($C_1$-$C_6$-alkoxy);
$R^2$ is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy;
or the N-oxides or the agriculturally acceptable salts thereof for combating phytopathogenic harmful fungi.

In one further preferred embodiment the invention relates to the use of compounds (I.a1), wherein A is phenyl. In one further preferred embodiment the invention relates to the use of compounds (I.a1), wherein A is phenyl and wherein the oxadiazol ring and the group Y=C—W are attached to the phenyl ring in para-position. In one further preferred embodiment the invention relates to the use of compounds (I.a1), wherein A is phenyl and wherein the oxadiazol ring and the group Y=C—W are attached to the phenyl ring in meta-position.

In one further preferred embodiment the invention relates to the use of compounds (I.a1), wherein A is pyridinyl. In one further preferred embodiment the invention relates to the use of compounds of formula (I.a1), wherein A is pyridinyl and wherein the oxadiazol ring and the group Y=C—W are attached to the pyridinyl ring in para-position. In one further preferred embodiment the invention relates to the use of compounds (I.a1), wherein A is pyridinyl and wherein the oxadiazol ring and the group Y=C—W are attached to the pyridinyl ring in meta-position.

In one further preferred embodiment the invention relates to the use of compounds (I.a1), wherein A is thienyl and wherein the oxadiazol ring and the group Y=C—W are attached to the thienyl ring in 2,5-position. In one further preferred embodiment the invention relates to the use of compounds (I.a1), wherein A is thienyl and wherein the oxadiazol ring and the group Y=C—W are attached to the thienyl ring in 3,5-position or 5,3-position.

In another preferred embodiment the invention relates to the use of compounds (I.a2) of formula I, wherein
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and alicyclic moieties are unsubstituted or substituted by 1, 2, 3 or 4 identical or different groups $R^a$; wherein
$R^a$ is halogen, cyano, $C_1$-$C_6$-alkyl, $C_1$-$C_6$-alkoxy or $C_3$-$C_8$-cycloalkyl;
Y is O;
W is $NR^1R^2$;
$R^1$ is hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)—($C_1$-$C_6$-alkyl) or C(=O)—($C_1$-$C_6$-alkoxy);
$R^2$ is phenyl, which is unsubstituted or substituted by 1, 2, 3 or up to the maximum possible number of identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy;
or the N-oxides or the agriculturally acceptable salts thereof for combating phytopathogenic harmful fungi.

In one further preferred embodiment the invention relates to the use of compounds (I.a2), wherein A is phenyl. In one further preferred embodiment the invention relates to the use of compounds (I.a2), wherein A is phenyl and wherein the oxadiazol ring and the group Y=C—W are attached to the phenyl ring in para-position. In one further preferred embodiment the invention relates to the use of compounds (I.a2), wherein A is phenyl and wherein the oxadiazol ring and the group Y=C—W are attached to the phenyl ring in meta-position.

In one further preferred embodiment the invention relates to the use of compounds (I.a2), wherein A is pyridinyl. In one further preferred embodiment the invention relates to the use of compounds (I.a2), wherein A is pyridinyl and wherein the oxadiazol ring and the group Y=C—W are attached to the pyridinyl ring in para-position. In one further preferred embodiment the invention relates to the use of compounds (I.a2), wherein A is pyridinyl and wherein the oxadiazol ring and the group Y=C—W are attached to the pyridinyl ring in meta-position.

In one further preferred embodiment the invention relates to the use of compounds (I.a2), wherein A is thienyl and wherein the oxadiazol ring and the group Y=C—W are attached to the thienyl ring in 2,5-position. In one further preferred embodiment the invention relates to the use of compounds (I.a2), wherein A is thienyl and wherein the oxadiazol ring and the group Y=C—W are attached to the thienyl ring in 3,5-position or 5,3-position.

In yet another preferred embodiment the invention relates to the use of compounds (I.a3) of formula I, wherein
A is phenyl, pyridinyl or thienyl; and wherein the cyclic groups A are unsubstituted or substituted by 1 or 2 identical or different groups $R^A$; wherein $R^A$ is halogen, cyano, $C_1$-$C_6$-alkyl, $C_1$-$C_6$-haloalkyl, $C_1$-$C_6$-alkoxy or $C_1$-$C_6$-haloalkoxy;

Y is O;

W is $NR^1R^2$;

$R^1$ is hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C(=O)$—($C_1$-$C_6$-alkyl) or $C(=O)$—($C_1$-$C_6$-alkoxy);

$R^2$ is phenyl, which is unsubstituted or substituted by 1, 2, 3 or up to the maximum possible number of identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy;

or the N-oxides or the agriculturally acceptable salts thereof for combating phytopathogenic harmful fungi.

In one further preferred embodiment the invention relates to the use of compounds (I.a3), wherein A is phenyl. In one further preferred embodiment the invention relates to the use of compounds (I.a3), wherein A is phenyl and wherein the oxadiazol ring and the group Y=C—W are attached to the phenyl ring in para-position. In one further preferred embodiment the invention relates to the use of compounds (I.a3), wherein A is phenyl and wherein the oxadiazol ring and the group Y=C—W are attached to the phenyl ring in meta-position.

In one further preferred embodiment the invention relates to the use of compounds (I.a3), wherein A is pyridinyl. In one further preferred embodiment the invention relates to the use of compounds (I.a3), wherein A is pyridinyl and wherein the oxadiazol ring and the group Y=C—W are attached to the pyridinyl ring in para-position. In one further preferred embodiment the invention relates to the use of compounds (I.a3), wherein A is pyridinyl and wherein the oxadiazol ring and the group Y=C—W are attached to the pyridinyl ring in meta-position.

In one further preferred embodiment the invention relates to the use of compounds (I.a3), wherein A is thienyl and wherein the oxadiazol ring and the group Y=C—W are attached to the thienyl ring in 2,5-position. In one further preferred embodiment the invention relates to the use of compounds (I.a3), wherein A is thienyl and wherein the oxadiazol ring and the group Y=C—W are attached to the thienyl ring in 3,5-position or 5,3-position.

In yet another preferred embodiment the invention relates to the use of compounds (I.a4) of formula I, wherein A is phenyl, pyridinyl or thienyl; and wherein the cyclic groups A are unsubstituted or substituted by 1 or 2 identical or different groups $R^A$; wherein $R^A$ is halogen, cyano, $C_1$-$C_6$-alkyl, $C_1$-$C_6$-haloalkyl, $C_1$-$C_6$-alkoxy or $C_1$-$C_6$-haloalkoxy;

Y is O;

W is $NR^1R^2$;

$R^1$ is hydrogen, $C_1$-$C_6$-alkyl, $C_2$-$C_6$-alkenyl or $C_2$-$C_6$-alkynyl;

$R^2$ is phenyl, which is unsubstituted or substituted by 1, 2, 3 or up to the maximum possible number of identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy;

or the N-oxides or the agriculturally acceptable salts thereof for combating phytopathogenic harmful fungi.

In one further preferred embodiment the invention relates to the use of compounds (I.a4), wherein A is phenyl. In one further preferred embodiment the invention relates to the use of compounds (I.a4), wherein A is phenyl and wherein the oxadiazol ring and the group Y=C—W are attached to the phenyl ring in para-position. In one further preferred embodiment the invention relates to the use of compounds (I.a4), wherein A is phenyl and wherein the oxadiazol ring and the group Y=C—W are attached to the phenyl ring in meta-position.

In one further preferred embodiment the invention relates to the use of compounds (I.a4), wherein A is pyridinyl. In one further preferred embodiment the invention relates to the use of compounds (I.a4), wherein A is pyridinyl and wherein the oxadiazol ring and the group Y=C—W are attached to the pyridinyl ring in para-position. In one further preferred embodiment the invention relates to the use of compounds (I.a4), wherein A is pyridinyl and wherein the oxadiazol ring and the group Y=C—W are attached to the pyridinyl ring in meta-position.

In one further preferred embodiment the invention relates to the use of compounds (I.a4), wherein A is thienyl and wherein the oxadiazol ring and the group Y=C—W are attached to the thienyl ring in 2,5-position. In one further preferred embodiment the invention relates to the use of compounds (I.a4), wherein A is thienyl and wherein the oxadiazol ring and the group Y=C—W are attached to the thienyl ring in 3,5-position or 5,3-position.

In one further preferred embodiment the invention relates to the use of compounds (I.a5) of formula I, wherein A is phenyl, pyridinyl or thienyl; and wherein the cyclic groups A are unsubstituted or substituted by 1 or 2 identical or different groups $R^A$; wherein $R^A$ is halogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and alicyclic moieties are unsubstituted or substituted by 1, 2, 3 or 4 identical or different groups $R^a$; wherein $R^a$ is halogen, cyano, $C_1$-$C_6$-alkyl, $C_1$-$C_6$-alkoxy or $C_3$-$C_8$-cycloalkyl;

Y is O;

W is $NR^1R^2$;

$R^1$ and $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl or $C_3$-$C_6$-cycloalkenyl; and wherein the alicyclic and the cyclic groups are unsubstituted or substituted by 1, 2, 3 or up to the maximum possible number of identical or different groups $R^{1a}$ as defined or preferably defined herein;

or the N-oxides or the agriculturally acceptable salts thereof for combating phytopathogenic harmful fungi.

In one further preferred embodiment the invention relates to the use of compounds (I.a5), wherein A is phenyl. In one further preferred embodiment the invention relates to the use of compounds (I.a5), wherein A is phenyl and wherein the oxadiazol ring and the group Y=C—W are attached to the phenyl ring in para-position. In one further preferred embodiment the invention relates to the use of compounds (I.a5), wherein A is phenyl and wherein the oxadiazol ring and the group Y=C—W are attached to the phenyl ring in meta-position.

In one further preferred embodiment the invention relates to the use of compounds (I.a5), wherein A is pyridinyl. In one further preferred embodiment the invention relates to the use of compounds (I.a5), wherein A is pyridinyl and wherein the oxadiazol ring and the group Y=C—W are attached to the pyridinyl ring in para-position. In one further preferred embodiment the invention relates to the use of compounds (I.a5), wherein A is pyridinyl and wherein the oxadiazol ring and the group Y=C—W are attached to the pyridinyl ring in meta-position.

In one further preferred embodiment the invention relates to the use of compounds (I.a5), wherein A is thienyl and wherein the oxadiazol ring and the group Y=C—W are attached to the thienyl ring in 2,5-position. In one further preferred embodiment the invention relates to the use of compounds (I.a5), wherein A is thienyl and wherein the oxadiazol ring and the group Y=C—W are attached to the thienyl ring in 3,5-position or 5,3-position.

In yet another preferred embodiment the invention relates to the use of compounds (I.a6) of formula I, wherein
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-haloalkyl, $C_1$-$C_6$-alkoxy or $C_1$-$C_6$-haloalkoxy;
Y is O;
W is $NR^1R^2$;
$R^1$ and $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl or $C_3$-$C_6$-cycloalkenyl;
or the N-oxides or the agriculturally acceptable salts thereof for combating phytopathogenic harmful fungi.

In one further preferred embodiment the invention relates to the use of compounds (I.a6), wherein A is phenyl. In one further preferred embodiment the invention relates to the use of compounds (I.a6), wherein A is phenyl and wherein the oxadiazol ring and the group Y=C—W are attached to the phenyl ring in para-position. In one further preferred embodiment the invention relates to the use of compounds (I.a6), wherein A is phenyl and wherein the oxadiazol ring and the group Y=C—W are attached to the phenyl ring in meta-position.

In one further preferred embodiment the invention relates to the use of compounds (I.a6), wherein A is pyridinyl. In one further preferred embodiment the invention relates to the use of compounds (I.a6), wherein A is pyridinyl and wherein the oxadiazol ring and the group Y=C—W are attached to the pyridinyl ring in para-position. In one further preferred embodiment the invention relates to the use of compounds (I.a6), wherein A is pyridinyl and wherein the oxadiazol ring and the group Y=C—W are attached to the pyridinyl ring in meta-position.

In one further preferred embodiment the invention relates to the use of compounds (I.a6), wherein A is thienyl and wherein the oxadiazol ring and the group Y=C—W are attached to the thienyl ring in 2,5-position. In one further preferred embodiment the invention relates to the use of compounds (I.a6), wherein A is thienyl and wherein the oxadiazol ring and the group Y=C—W are attached to the thienyl ring in 3,5-position or 5,3-position.

In one further preferred embodiment the invention relates to the use of compounds (I.a7) of formula I, wherein
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and alicyclic moieties are unsubstituted or substituted by 1, 2, 3 or 4 identical or different groups $R^a$; wherein
$R^a$ is halogen, cyano, $C_1$-$C_6$-alkyl, $C_1$-$C_6$-alkoxy or $C_3$-$C_8$-cycloalkyl;
Y is O;
W is $NR^1R^2$;
$R^1$ and $R^2$ together with the nitrogen atom to which they are bound form a saturated or partially unsaturated 3- to 6-membered heterocycle, wherein the heterocycle includes beside one nitrogen atom and carbon atoms 1, 2 or 3 heteroatoms independently selected from N, O and S as ring member atoms; and wherein one or two $CH_2$ groups of the carbo- or heterocycle may be replaced by one or two groups independently selected from the group of C(=O) and C(=S); and wherein the heterocycle is unsubstituted or carries 1, 2, 3, 4 or up to the maximum possible number of identical or different groups $R^{1a}$ as defined or preferably defined herein;
or the N-oxides or the agriculturally acceptable salts thereof for combating phytopathogenic harmful fungi.

In one further preferred embodiment the invention relates to the use of compounds (I.a7), wherein A is phenyl. In one further preferred embodiment the invention relates to the use of compounds (I.a7), wherein A is phenyl and wherein the oxadiazol ring and the group Y=C—W are attached to the phenyl ring in para-position. In one further preferred embodiment the invention relates to the use of compounds (I.a7), wherein A is phenyl and wherein the oxadiazol ring and the group Y=C—W are attached to the phenyl ring in meta-position.

In one further preferred embodiment the invention relates to the use of compounds (I.a7), wherein A is pyridinyl. In one further preferred embodiment the invention relates to the use of compounds (I.a7), wherein A is pyridinyl and wherein the oxadiazol ring and the group Y=C—W are attached to the pyridinyl ring in para-position. In one further preferred embodiment the invention relates to the use of compounds (I.a7), wherein A is pyridinyl and wherein the oxadiazol ring and the group Y=C—W are attached to the pyridinyl ring in meta-position.

In one further preferred embodiment the invention relates to the use of compounds (I.a7), wherein A is thienyl and wherein the oxadiazol ring and the group Y=C—W are attached to the thienyl ring in 2,5-position. In one further preferred embodiment the invention relates to the use of compounds (I.a7), wherein A is thienyl and wherein the oxadiazol ring and the group Y=C—W are attached to the thienyl ring in 3,5-position or 5,3-position.

In yet another preferred embodiment the invention relates to the use of compounds (I.a8) of formula I, wherein
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-haloalkyl, $C_1$-$C_6$-alkoxy or $C_1$-$C_6$-haloalkoxy;
Y is O;
W is $NR^1R^2$;
$R^1$ and $R^2$ together with the nitrogen atom to which they are bound form a saturated or partially unsaturated 3- to 6-membered heterocycle, wherein the heterocycle includes beside one nitrogen atom and carbon atoms 1, 2 or 3 heteroatoms independently selected from N, O and S as ring member atoms; and wherein the heterocycle is unsubstituted or carries 1, 2, 3 or 4 identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy;
or the N-oxides or the agriculturally acceptable salts thereof for combating phytopathogenic harmful fungi.

In one further preferred embodiment the invention relates to the use of compounds (I.a8), wherein A is phenyl. In one further preferred embodiment the invention relates to the use of compounds (I.a8), wherein A is phenyl and wherein the oxadiazol ring and the group Y=C—W are attached to the phenyl ring in para-position. In one further preferred embodiment the invention relates to the use of compounds (I.a8), wherein A is phenyl and wherein the oxadiazol ring and the group Y=C—W are attached to the phenyl ring in meta-position.

In one further preferred embodiment the invention relates to the use of compounds (I.a8), wherein A is pyridinyl. In one further preferred embodiment the invention relates to the use of compounds (I.a8), wherein A is pyridinyl and wherein the oxadiazol ring and the group Y=C—W are attached to the pyridinyl ring in para-position. In one further preferred embodiment the invention relates to the use of compounds (I.a8), wherein A is pyridinyl and wherein the oxadiazol ring and the group Y=C—W are attached to the pyridinyl ring in meta-position.

In one further preferred embodiment the invention relates to the use of compounds (I.a8), wherein A is thienyl and wherein the oxadiazol ring and the group Y=C—W are attached to the thienyl ring in 2,5-position. In one further preferred embodiment the invention relates to the use of compounds (I.a8), wherein A is thienyl and wherein the oxadiazol ring and the group Y=C—W are attached to the thienyl ring in 3,5-position or 5,3-position.

In one further embodiment the invention relates to the use of compounds (I.b1) of formula I, wherein:
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and alicyclic moieties are unsubstituted or substituted by 1, 2, 3 or 4 identical or different groups $R^a$; wherein
$R^a$ is halogen, cyano, $C_1$-$C_6$-alkyl, $C_1$-$C_6$-alkoxy or $C_3$-$C_8$-cycloalkyl;
Y is O;
W is $OR^3$;
$R^3$ is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy;
or the N-oxides or the agriculturally acceptable salts thereof for combating phytopathogenic harmful fungi.

In one further preferred embodiment the invention relates to the use of compounds (I.b1), wherein A is phenyl. In one further preferred embodiment the invention relates to the use of compounds (I.b1), wherein A is phenyl and wherein the oxadiazol ring and the group Y=C—W are attached to the phenyl ring in para-position. In one further preferred embodiment the invention relates to the use of compounds (I.b1), wherein A is phenyl and wherein the oxadiazol ring and the group Y=C—W are attached to the phenyl ring in meta-position.

In one further preferred embodiment the invention relates to the use of compounds (I.b1), wherein A is pyridinyl. In one further preferred embodiment the invention relates to the use of compounds (I.b1), wherein A is pyridinyl and wherein the oxadiazol ring and the group Y=C—W are attached to the pyridinyl ring in para-position. In one further preferred embodiment the invention relates to the use of compounds (I.b1), wherein A is pyridinyl and wherein the oxadiazol ring and the group Y=C—W are attached to the pyridinyl ring in meta-position.

In one further preferred embodiment the invention relates to the use of compounds (I.b1), wherein A is thienyl and wherein the oxadiazol ring and the group Y=C—W are attached to the thienyl ring in 2,5-position. In one further preferred embodiment the invention relates to the use of compounds (I.b1), wherein A is thienyl and wherein the oxadiazol ring and the group Y=C—W are attached to the thienyl ring in 3,5-position or 5,3-position.

In one further preferred embodiment the invention relates to the use of compounds (I.b2) of formula I, wherein
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and alicyclic moieties are unsubstituted or substituted by 1, 2, 3 or 4 identical or different groups $R^a$; wherein
$R^a$ is halogen, cyano, $C_1$-$C_6$-alkyl, $C_1$-$C_6$-alkoxy or $C_3$-$C_8$-cycloalkyl;
Y is O;
W is $OR^3$;
$R^3$ is phenyl, which is unsubstituted or substituted by 1, 2, 3 or up to the maximum possible number of identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy;
or the N-oxides or the agriculturally acceptable salts thereof for combating phytopathogenic harmful fungi.

In one further preferred embodiment the invention relates to the use of compounds (I.b2), wherein A is phenyl. In one further preferred embodiment the invention relates to the use of compounds (I.b2), wherein A is phenyl and wherein the oxadiazol ring and the group Y=C—W are attached to the phenyl ring in para-position. In one further preferred embodiment the invention relates to the use of compounds (I.b2), wherein A is phenyl and wherein the oxadiazol ring and the group Y=C—W are attached to the phenyl ring in meta-position.

In one further preferred embodiment the invention relates to the use of compounds (I.b2), wherein A is pyridinyl. In one further preferred embodiment the invention relates to the use of compounds (I.b2), wherein A is pyridinyl and wherein the oxadiazol ring and the group Y=C—W are attached to the pyridinyl ring in para-position. In one further preferred embodiment the invention relates to the use of compounds (I.b2), wherein A is pyridinyl and wherein the oxadiazol ring and the group Y=C—W are attached to the pyridinyl ring in meta-position.

In one further preferred embodiment the invention relates to the use of compounds (I.b2), wherein A is thienyl and wherein the oxadiazol ring and the group Y=C—W are attached to the thienyl ring in 2,5-position. In one further preferred embodiment the invention relates to the use of compounds (I.b2), wherein A is thienyl and wherein the oxadiazol ring and the group Y=C—W are attached to the thienyl ring in 3,5-position or 5,3-position.

In one further preferred embodiment the invention relates to the use of compounds (I.b3) of formula I, wherein
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and alicyclic moieties are unsubstituted or substituted by 1, 2, 3 or 4 identical or different groups $R^a$; wherein
  $R^a$ is halogen, cyano, $C_1$-$C_6$-alkyl, $C_1$-$C_6$-alkoxy or $C_3$-$C_8$-cycloalkyl;
Y is O;
W is $OR^3$;
$R^3$ is $C_2$-$C_6$-alkyl, $C_2$-$C_6$-alkenyl, $C_2$-$C_6$-alkynyl, $C_3$-$C_6$-cycloalkyl, $C_3$-$C_6$-cycloalkenyl; and wherein the alicyclic and the cyclic groups are unsubstituted or substituted by 1, 2, 3 or up to the maximum possible number of identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy;
or the N-oxides or the agriculturally acceptable salts thereof for combating phytopathogenic harmful fungi.

In one further preferred embodiment the invention relates to the use of compounds (I.b3), wherein A is phenyl. In one further preferred embodiment the invention relates to the use of compounds (I.b3), wherein A is phenyl and wherein the oxadiazol ring and the group Y=C—W are attached to the phenyl ring in para-position. In one further preferred embodiment the invention relates to the use of compounds (I.b3), wherein A is phenyl and wherein the oxadiazol ring and the group Y=C—W are attached to the phenyl ring in meta-position.

In one further preferred embodiment the invention relates to the use of compounds (I.b3), wherein A is pyridinyl. In one further preferred embodiment the invention relates to the use of compounds (I.b3), wherein A is pyridinyl and wherein the oxadiazol ring and the group Y=C—W are attached to the pyridinyl ring in para-position. In one further preferred embodiment the invention relates to the use of compounds (I.b3), wherein A is pyridinyl and wherein the oxadiazol ring and the group Y=C—W are attached to the pyridinyl ring in meta-position.

In one further preferred embodiment the invention relates to the use of compounds (I.b3), wherein A is thienyl and wherein the oxadiazol ring and the group Y=C—W are attached to the thienyl ring in 2,5-position. In one further preferred embodiment the invention relates to the use of compounds (I.b3), wherein A is thienyl and wherein the oxadiazol ring and the group Y=C—W are attached to the thienyl ring in 3,5-position or 5,3-position.

In one further preferred embodiment the invention relates to the use of compounds (I.b4) of formula I, wherein
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-haloalkyl, $C_1$-$C_6$-alkoxy or $C_1$-$C_6$-haloalkoxy;
Y is O;
W is $OR^3$;
$R^3$ is phenyl, which is unsubstituted or substituted by 1, 2, 3 or up to the maximum possible number of identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy;
or the N-oxides or the agriculturally acceptable salts thereof for combating phytopathogenic harmful fungi.

In one further preferred embodiment the invention relates to the use of compounds (I.b4), wherein A is phenyl. In one further preferred embodiment the invention relates to the use of compounds (I.b4), wherein A is phenyl and wherein the oxadiazol ring and the group Y=C—W are attached to the phenyl ring in para-position. In one further preferred embodiment the invention relates to the use of compounds (I.b4), wherein A is phenyl and wherein the oxadiazol ring and the group Y=C—W are attached to the phenyl ring in meta-position.

In one further preferred embodiment the invention relates to the use of compounds (I.b4), wherein A is pyridinyl. In one further preferred embodiment the invention relates to the use of compounds (I.b4), wherein A is pyridinyl and wherein the oxadiazol ring and the group Y=C—W are attached to the pyridinyl ring in para-position. In one further preferred embodiment the invention relates to the use of compounds (I.b4), wherein A is pyridinyl and wherein the oxadiazol ring and the group Y=C—W are attached to the pyridinyl ring in meta-position.

In one further preferred embodiment the invention relates to the use of compounds (I.b4), wherein A is thienyl and wherein the oxadiazol ring and the group Y=C—W are attached to the thienyl ring in 2,5-position. In one further preferred embodiment the invention relates to the use of compounds (I.b4), wherein A is thienyl and wherein the oxadiazol ring and the group Y=C—W are attached to the thienyl ring in 3,5-position or 5,3-position.

In one further preferred embodiment the invention relates to the use of compounds (I.b5) of formula I, wherein
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-haloalkyl, $C_1$-$C_6$-alkoxy or $C_1$-$C_6$-haloalkoxy;
Y is O;
W is $OR^3$;
$R^3$ is $C_2$-$C_6$-alkyl, $C_2$-$C_6$-alkenyl, $C_2$-$C_6$-alkynyl, $C_3$-$C_6$-cycloalkyl, $C_3$-$C_6$-cycloalkenyl; or the N-oxides or the agriculturally acceptable salts thereof for combating phytopathogenic harmful fungi.

In one further preferred embodiment the invention relates to the use of compounds (I.b5) of formula I, wherein
A is phenyl, pyridinyl or thienyl; and wherein the cyclic groups A are unsubstituted or substituted by 1 or 2 identical or different groups $R^A$; wherein
$R^A$ is halogen, cyano, $C_1$-$C_6$-alkyl, $C_1$-$C_6$-haloalkyl, $C_1$-$C_6$-alkoxy or $C_1$-$C_6$-haloalkoxy;
Y is O;
W is $OR^3$;
$R^3$ is $C_3$-$C_6$-cycloalkyl, $C_3$-$C_6$-cycloalkenyl; and wherein the cyclic groups $R^3$ are unsubstituted or substituted by 1, 2, 3 or up to the maximum possible number of identical or different groups $R^{3a}$ as defined or preferably defined herein;
or the N-oxides or the agriculturally acceptable salts thereof for combating phytopathogenic harmful fungi.

In one further preferred embodiment the invention relates to the use of compounds (I.b5), wherein A is phenyl. In one further preferred embodiment the invention relates to the use of compounds (I.b5), wherein A is phenyl and wherein the oxadiazol ring and the group Y=C—W are attached to the phenyl ring in para-position. In one further preferred embodiment the invention relates to the use of compounds (I.b5), wherein A is phenyl and wherein the oxadiazol ring and the group Y=C—W are attached to the phenyl ring in meta-position.

In one further preferred embodiment the invention relates to the use of compounds (I.b5), wherein A is pyridinyl. In one further preferred embodiment the invention relates to the use of compounds (I.b5), wherein A is pyridinyl and wherein the oxadiazol ring and the group Y=C—W are attached to the pyridinyl ring in para-position. In one further preferred embodiment the invention relates to the use of compounds (I.b5), wherein A is pyridinyl and wherein the oxadiazol ring and the group Y=C—W are attached to the pyridinyl ring in meta-position.

In one further preferred embodiment the invention relates to the use of compounds (I.b5), wherein A is thienyl and wherein the oxadiazol ring and the group Y=C—W are attached to the thienyl ring in 2,5-position. In one further preferred embodiment the invention relates to the use of compounds (I.b5), wherein A is thienyl and wherein the oxadiazol ring and the group Y=C—W are attached to the thienyl ring in 3,5-position or 5,3-position.

According to one embodiment the cyclic groups A in compounds I.a1 to I.a8 and I.b1 to I.b5 are unsubstituted or substituted by 1 group $R^4$ as respectively defined for each of those compounds. According to one embodiment the cyclic groups A in compounds I.a1 to I.a8 and I.b1 to I.b5 are substituted by 1 group $R^4$ as respectively defined for each of those compounds.

According to one embodiment the cyclic groups A in compounds I.a1 to I.a8 and I.b1 to I.b5 are substituted by 2 groups $R^4$ as respectively defined for each of those compounds. According to one embodiment the cyclic groups A in compounds I.a1 to I.a8 and I.b1 to I.b5 are unsubstituted.

The compounds of formula I can be prepared according to methods or in analogy to methods as described in WO 2013/008162 A1 and WO 2013/080120 A1, wherein A is, for example, a phenyl ring. The synthesis takes advantage of readily available starting materials that are known, commercially available or may be prepared according to conventional procedures starting from known compounds.

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti).

Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e.g. conifers; and on the plant propagation material, such as seeds, and the crop material of these plants; particularly the compounds of the formula I and the compositions according to the invention are important in the control of phytopathogenic fungi on soybeans and on the plant propagation material, such as seeds, and the crop material of soybeans.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil.

These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors.

These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above.

These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the Mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The compounds I and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Altemaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. altemata*), tomatoes (e.g. *A. solani* or *A. altemata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botrifotinia fucliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitipona* (syn. *Phellinus*) *punctata, F. mediterranea, Phaeomoniella chlamydospora* (earlier *Phaeoacremonium chlamydosporum*), *Phaeoacremonium aleophilum* and/or *Botlyosphaeria obtusa; Elsinoe* spp. on pome fruits (*E. pyn*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohllum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* (f. sp. glycines now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuror*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemlleia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans* late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni*(*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, R. so/an/(sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. roifsii* or *S. sclerotiorum*); *Septoria* spp. on various plants, e.g. *S. glycines* (brown spot) on soybeans, *S. tritici* (*Septoria* blotch) on wheat and S. (syn. *Stagonospora*) *nodorum* (*Stagonospora* blotch) on cereals; *Uncinuia* (syn. *Erysiphe*) *necator* (powdery mildew, anamorph: *Oidium*

*tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustllago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, are also suitable for controlling harmful fungi in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecllomyces* spp. and Zygomycetes such as *Mucor* spp., and in addition in the protection of stored products and harvest the following yeast fungi are worthy of note: *Candida* spp. and *Saccharomyces cerevisae*.

In a preferred embodiment the compounds I and compositions thereof, respectively, are particularly suitable for controlling the following plant diseases: *Phakopsora pachyrhizi* and *P. meibomiae* (soybean rust) on soybeans.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubenmann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzyl alcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methyl pyrrolidone, fatty acid dimethyl amides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters.

Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide.

Examples of N-substituted fatty acid amides are fatty acid glucamides or fatty acid alkanolamides. Examples of esters are fatty acid esters, glycerol esters or monoglycerides.

Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target.

Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:
i) Water-Soluble Concentrates (SL, LS)
10-60 wt % of a compound I and 5-15 wt % wetting agent (e.g. alcohol alkoxylates) are dissolved in water and/or in a water-soluble solvent (e.g. alcohols) ad 100 wt %. The active substance dissolves upon dilution with water.
ii) Dispersible Concentrates (DC)
5-25 wt % of a compound I and 1-10 wt % dispersant (e.g. polyvinyl pyrrolidone) are dissolved in organic solvent (e.g. cyclohexanone) ad 100 wt %. Dilution with water gives a dispersion.
iii) Emulsifiable Concentrates (EC)
15-70 wt % of a compound I and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinyl alcohol) is added.

vi) Water-Dispersible Granules and Water-Soluble Granules (WG, SG)

50-80 wt % of a compound I are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e.g. sodium lignosulfonate), 1-5 wt % thickener (e.g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e.g. fatty acid dimethyl amide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e.g. finely divided kaolin) ad 100 wt %.

xii) Granules (GR, FG)

0.5-30 wt % of a compound I is ground finely and associated with solid carrier (e.g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e.g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods.

Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e.g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II, or component 2) (e.g. pesticidally-active substances), in conjunction with which the compounds I can be used, is intended to illustrate the possible combinations but does not limit them:

A) Respiration inhibitors
  Inhibitors of complex III at $Q_o$ site (e.g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)pyrazol-3-yl]oxymethyl]phenyl]-4-methyl-tetrazol-5-one instead of 1-[3-chloro-2-[[[1-(4-chlorophenyl)-1H-pyrazol-3-yl]oxy]methyl]phenyl]-1,4-dihydro-4-methyl-5H-tetrazol-5-one (A.1.23), (Z,2E)-5-[1-(2,4-dichlorophenyl)-1H-pyrazol-3-yl]oxy-2-(methoxyimino)-N,3-dimethyl-pent-3-enamide (A.1.24), (Z,2E)-5-[1-(4-chlorophenyl)-1H-pyrazol-3-yl]oxy-2-(methoxyimino)-N,3-dimethyl-pent-3-enamide (A.1.25), (Z,2E)-5-[1-(4-chloro-2-fluoro-phenyl)pyrazol-3-yl]oxy-2-methoxyimino-N,3-dimethyl-pent-3-enamide (A.1.26), 1-[3-bromo-2-[[1-(4-chlorophenyl)pyrazol-3-yl]oxymethyl]phenyl]-4-methyl-tetrazol-5-one (A.1.27), 1-[2-[[1-(4-chlorophenyl)pyrazol-3-yl]oxymethyl]-3-methyl-phenyl]-4-methyl-tetrazol-5-one (A.1.28), 1-[2-[[1-(4-chlorophenyl)pyrazol-3-yl]oxymethyl]-3-fluoro-phenyl]-4-methyl-tetrazol-5-one (A.1.29), 1-[2-[[1-(2,4-dichlorophenyl)pyrazol-3-yl]oxymethyl]-3-fluoro-phenyl]-4-methyl-tetrazol-5-one (A.1.30), 1-[2-[[4-(4-chlorophenyl)thiazol-2-yl]-oxymethyl]-3-methyl-phenyl]-4-methyl-tetrazol-5-one (A.1.31), 1-[3-chloro-2-[[4-(p-tolyl)thiazol-2-yl]oxymethyl]phenyl]-4-methyl-tetrazol-5-one (A.1.32), 1-[3-cyclopropyl-2-[[2-methyl-4-(1-methylpyrazol-3-yl)phenoxy]methyl]phenyl]-4-methyl-tetrazol-5-one (A.1.33);

inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate (A.2.3), [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy)methoxy]-4-methoxypicolinamido]-6-methyl-4,9-dioxo-1,5-dioxonan-7-yl isobutyrate (A.2.8);

inhibitors of complex II (e.g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethylbutyl)-phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4- carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methyl-ethyl]-3-(difluoromethyl)-1-methyl-pyrazole-4-carboxamide (A.3.27);

other respiration inhibitors (e.g. complex I, uncouplers): diflumetorim (A.4.1), (5,8-difluoro-quinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol biosynthesis inhibitors (SBI fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S; 3R)-3-(2-chlorophenyl)-2-(2,4-difluorophenyl)-oxiranylmethyl]-5-thiocyanato-1H-[1,2,4]triazolo (B.1.31), 2-[rel-(2S,3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-isocyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyl)isoxazol-4-yl]-(3-pyridylmethanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic acid synthesis inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of cell division and cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of amino acid and protein synthesis methionine synthesis inhibitors (anilino-pyrimidines): cyprodinil (E.1.1), mepanipyrim (E.1.2), pyrimethanil (E.1.3);

protein synthesis inhibitors: blasticidin-S(E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal transduction inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and membrane synthesis inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7); phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenypethanesulfonyl)-but-2-yl) carbamic acid-(4-fluorophenyl) ester (G.3.8);

compounds affecting cell membrane permeability and fatty acids: propamocarb (G.4.1);

fatty acid amide hydrolase inhibitors: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action
- inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);
- thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);
- organochlorine compounds (e.g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methyl-benzenesulfonamide (H.3.12);
- guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c]dipyrrole-1,3,5,7(2H,6H)-tetraone (H.4.10);

I) Cell wall synthesis inhibitors
- inhibitors of glucan synthesis: validamycin (I.1.1), polyoxin B (I.1.2); melanin synthesis inhibitors: pyroquilon (I.2.1), tricyclazole (I.2.2), carpropamid (I.2.3), dicyclomet (I.2.4), fenoxanil (I.2.5);

J) Plant defence inducers
- acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown mode of action
- bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yl-oxy)phenyl]-4,5-dihydro-1,2-oxazol-3-yl}-1,3-thiazol-2-yl)piperidin-1-yl]ethanone (K.1.29), N-(cyclopropylmethoxyimino-(6-difluoro-methoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethyl-silanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl)cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48);

M) Growth regulators
abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides
- acetamides: acetochlor (N.1.1), alachlor, butachlor, dimethachlor, dimethenamid (N.1.2), flufenacet (N.1.3), mefenacet (N.1.4), metolachlor (N.1.5), metazachlor (N.1.6), napropamide, naproanilide, pethoxamid, pretilachlor, propachlor, thenylchlor;
- amino acid derivatives: bilanafos, glyphosate (N.2.1), glufosinate (N.2.2), sulfosate (N.2.3);
- aryloxyphenoxypropionates: clodinafop (N.3.1), cyhalofop-butyl, fenoxaprop (N.3.2), fluazifop (N.3.3), haloxyfop (N.3.4), metamifop, propaquizafop, quizalofop, quizalofop-P-tefuryl;
- Bipyridyls: diquat, paraquat (N.4.1);
- (thio)carbamates: asulam, butylate, carbetamide, desmedipham, dimepiperate, eptam (EPTC), esprocarb, molinate, orbencarb, phenmedipham (N.5.1), prosulfocarb, pyributicarb, thiobencarb, triallate;
- cyclohexanediones: butroxydim, clethodim (N.6.1), cycloxydim (N.6.2), profoxydim (N.6.3), sethoxydim (N.6.4), tepraloxydim (N.6.5), tralkoxydim;
- dinitroanilines: benfluralin, ethalfluralin, oryzalin, pendimethalin (N.7.1), prodiamine (N.7.2), trifluralin (N.7.3);
- diphenyl ethers: acifluorfen (N.8.1), aclonifen, bifenox, diclofop, ethoxyfen, fomesafen, lactofen, oxyfluorfen;
- hydroxybenzonitriles: bomoxynil (N.9.1), dichlobenil, ioxynil;

imidazolinones: imazamethabenz, imazamox (N.10.1), imazapic (N.10.2), imazapyr (N.10.3), imazaquin (N.10.4), imazethapyr (N.10.5);

phenoxy acetic acids: clomeprop, 2,4-dichlorophenoxyacetic acid (2,4-D) (N.11.1), 2,4-DB, dichlorprop, MCPA, MCPA-thioethyl, MCPB, Mecoprop;

pyrazines: chloridazon (N.11.1), flufenpyr-ethyl, fluthiacet, norflurazon, pyridate;

pyridines: aminopyralid, clopyralid (N.12.1), diflufenican, dithiopyr, fluridone, fluroxypyr (N.12.2), picloram (N.12.3), picolinafen (N.12.4), thiazopyr;

sulfonyl ureas: amidosulfuron, azimsulfuron, bensulfuron (N.13.1), chlorimuron-ethyl (N.13.2), chlorsulfuron, cinosulfuron, cyclosulfamuron (N.13.3), ethoxysulfuron, flazasulfuron, flucetosulfuron, flupyrsulfuron, foramsulfuron, halosulfuron, imazosulfuron, iodosulfuron (N.13.4), mesosulfuron (N.13.5), metazosulfuron, metsulfuron-methyl (N.13.6), nicosulfuron (N.13.7), oxasulfuron, primisulfuron, prosulfuron, pyrazosulfuron, rimsulfuron (N.13.8), sulfometuron, sulfosulfuron, thifensulfuron, triasulfuron, tribenuron, trifloxysulfuron, triflusulfuron (N.13.9), tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine (N.14.1), cyanazine, dimethametryn, ethiozin, hexazinone (N.14.2), metamitron, metribuzin, prometryn, simazine, terbuthylazine, terbutryn, triaziflam, trifludimoxazin (N14.3);

ureas: chlorotoluron, daimuron, diuron (N.15.1), fluometuron, isoproturon, linuron, metha-benzthiazuron, tebuthiuron;

other acetolactate synthase inhibitors: bispyribac-sodium, cloransulam-methyl, diclosulam, florasulam (N.16.1), flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone (N.16.2), pyroxsulam;

others: amicarbazone, aminotriazole, anilofos, beflubutamid, benazolin, bencarbazone, benfluresate, benzofenap, bentazone (N.17.1), benzobicyclon, bicyclopyrone, bromacil, bromobutide, butafenacil, butamifos, cafenstrole, carfentrazone, cinidon-ethyl (N.17.2), chlorthal, cinmethylin (N.17.3), clomazone (N.17.4), cumyluron, cyprosulfamide, dicamba (N.17.5), difenzoquat, diflufenzopyr (N.17.6), *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac (N.17.7), quinmerac (N.17.8), mesotrione (N.17.9), methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil (N.17.10), sulcotrione (N.17.11), sulfentrazone, terbacil, tefuryltrione, tembotrione, thiencarbazone, topramezone (N.17.12), (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O) Insecticides organo(thio)phosphates: acephate (O.1.1), azamethiphos (O.1.2), azinphos-methyl (O.1.3), chlorpyrifos (O.1.4), chlorpyrifos-methyl (O.1.5), chlorfenvinphos (O.1.6), diazinon (O.1.7), dichlorvos (O.1.8), dicrotophos (O.1.9), dimethoate (O.1.10), disulfoton (O.1.11), ethion (O.1.12), fenitrothion (O.1.13), fenthion (O.1.14), isoxathion (O.1.15), malathion (O.1.16), methamidophos (O.1.17), methidathion (O.1.18), methyl-parathion (O.1.19), mevinphos (O.1.20), monocrotophos (O.1.21), oxydemeton-methyl (O.1.22), paraoxon (O.1.23), parathion (O.1.24), phenthoate (O.1.25), phosalone (O.1.26), phosmet (O.1.27), phosphamidon (O.1.28), phorate (O.1.29), phoxim (O.1.30), pirimiphos-methyl (O.1.31), profenofos (O.1.32), prothiofos (O.1.33), sulprophos (O.1.34), tetrachlorvinphos (O.1.35), terbufos (O.1.36), triazophos (O.1.37), trichlorfon (O.1.38);

carbamates: alanycarb (O.2.1), aldicarb (O.2.2), bendiocarb (O.2.3), benfuracarb (O.2.4), carbaryl (O.2.5), carbofuran (O.2.6), carbosulfan (O.2.7), fenoxycarb (O.2.8), furathiocarb (O.2.9), methiocarb (O.2.10), methomyl (O.2.11), oxamyl (O.2.12), pirimicarb (O.2.13), propoxur (O.2.14), thiodicarb (O.2.15), triazamate (O.2.16);

pyrethroids: allethrin (O.3.1), bifenthrin (O.3.2), cyfluthrin (O.3.3), cyhalothrin (O.3.4), cyphenothrin (O.3.5), cypermethrin (O.3.6), alpha-cypermethrin (O.3.7), beta-cypermethrin (O.3.8), zeta-cypermethrin (O.3.9), deltamethrin (O.3.10), esfenvalerate (O.3.11), etofenprox (O.3.11), fenpropathrin (O.3.12), fenvalerate (O.3.13), imiprothrin (O.3.14), lambda-cyhalothrin (O.3.15), permethrin (O.3.16), prallethrin (O.3.17), pyrethrin I and II (O.3.18), resmethrin (O.3.19), silafluofen (O.3.20), tau-fluvalinate (O.3.21), tefluthrin (O.3.22), tetramethrin (O.3.23), tralomethrin (O.3.24), transfluthrin (O.3.25), profluthrin (O.3.26), dimefluthrin (O.3.27);

insect growth regulators: a) chitin synthesis inhibitors: benzoylureas: chlorfluazuron (O.4.1), cyramazin (O.4.2), diflubenzuron (O.4.3), flucycloxuron (O.4.4), flufenoxuron (O.4.5), hexaflumuron (O.4.6), lufenuron (O.4.7), novaluron (O.4.8), teflubenzuron (O.4.9), triflumuron (O.4.10); buprofezin (O.4.11), diofenolan (O.4.12), hexythiazox (O.4.13), etoxazole (O.4.14), clofentazine (O.4.15); b) ecdysone antagonists: halofenozide (O.4.16), methoxyfenozide (O.4.17), tebufenozide (O.4.18), azadirachtin (O.4.19); c) juvenoids: pyriproxyfen (O.4.20), methoprene (O.4.21), fenoxycarb (O.4.22); d) lipid biosynthesis inhibitors: spirodiclofen (O.4.23), spiromesifen (O.4.24), spirotetramat (O.4.24);

nicotinic receptor agonists/antagonists compounds: clothianidin (O.5.1), dinotefuran (O.5.2), flupyradifurone (O.5.3), imidacloprid (O.5.4), thiamethoxam (O.5.5), nitenpyram (O.5.6), acetamiprid (O.5.7), thiacloprid (O.5.8), 1-2-chloro-thiazol-5-ylmethyl)-2-nitrimino-3,5-dimethyl-[1,3,5]triazinane (O.5.9);

GABA antagonist compounds: endosulfan (O.6.19, ethiprole (O.6.2), fipronil (O.6.3), vaniliprole (O.6.4), pyrafluprole (O.6.5), pyriprole (O.6.6), 5-amino-1-(2,6-dichloro-4-methyl-phenyl)-4-sulfinamoyl-1H-pyrazole-3-carbothioic acid amide (O.6.7); macrocyclic lactone insecticides: abamectin (O.7.1), emamectin (O.7.2), milbemectin (O.7.3), lepimectin (O.7.4), spinosad (O.7.5), spinetoram (O.7.6);

mitochondrial electron transport inhibitor (METI) I acaricides: fenazaquin (O.8.1), pyridaben (O.8.2), tebufenpyrad (O.8.3), tolfenpyrad (O.8.4), flufenerim (O.8.5);

METI II and III compounds: acequinocyl (O.9.1), fluacyprim (O.9.2), hydramethylnon (O.9.3);

Uncouplers: chlorfenapyr (O.10.1);

oxidative phosphorylation inhibitors: cyhexatin (O.11.1), diafenthiuron (O.11.2), fenbutatin oxide (O.11.3), propargite (O.11.4);

moulting disruptor compounds: cryomazine (O.12.1);

mixed function oxidase inhibitors: piperonyl butoxide (O.13.1);

sodium channel blockers: indoxacarb (O.14.1), metaflumizone (O.14.2);

ryanodine receptor inhibitors: chlorantraniliprole (O.15.1), cyantraniliprole (O.15.2), flu-bendiamide (O.15.3), N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide (O.15.4); N-[4-chloro-2-[(di-ethyl-lambda-4-sulfanylidene)carbamoyl]-6-methyl-phenyl]-2-(3-chloro-2-pyridyl)-5-(trifluoromethyl)pyrazole-3-carboxamide (O.15.5); N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide (O.15.6); N-[4,6-dichloro-2-[(di-2-propyl-lambda-4-sulfanylidene)carbamoyl]-phenyl]-2-(3-chloro-2-pyridyl)-5-(trifluoromethyl) pyrazole-3-carboxamide (O.15.7); N-[4,6-dichloro-2-[(diethyl-lambda-4-sulfanylidene)carbamoyl]-phenyl]-2-(3-chloro-2-pyridyl)-5-(difluoromethyl) pyrazole-3-carboxamide (O.15.8); N-[4,6-dibromo-2-[(di-2-propyl-lambda-4-sulfanylidene) carbamoyl]-phenyl]-2-(3-chloro-2-pyridyl)-5-(trifluoromethyl)pyrazole-3-carboxamide (O.15.9); N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide (O.15.10); N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide (O.15.11);

others: benclothiaz (O.16.1), bifenazate (O.16.2), artap (O.16.3), flonicamid (O.16.4), pyridalyl (O.16.5), pymetrozine (O.16.6), sulfur (O.16.7), thiocyclam (O.16.8), cyenopyrafen (O.16.9), flupyrazofos (O.16.10), cyflumetofen (O.16.11), amidoflumet (O.16.12), imicyafos (O.16.13), bistrifluron (O.16.14), pyrifluquinazon (O.16.15) and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]cyclopropaneacetic acid ester (O.16.16).

The active substances referred to as component 2, their preparation and their activity e.g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

The present invention furthermore relates to agrochemical mixtures comprising at least one compound I (component 1) and at least one further active substance useful for plant protection, e.g. selected from the groups A) to O) (component 2), in particular one further fungicide, e.g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e.g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In the binary mixtures and compositions according to the invention the weight ratio of the component 1) and the component 2) generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to a further embodiment of the binary mixtures and compositions thereof, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiment of the binary mixtures and compositions thereof, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

Preference is also given to mixtures comprising as component 2) at least one active substance selected from group A), which is particularly selected from (A.1.1), (A.1.4), (A.1.8), (A.1.9), (A.1.12), (A.1.13), (A.1.14), (A.1.17), (A.1.19), (A.1.21), (A.2.1), (A.2.2), (A.2.8), (A.3.2), (A.3.3), (A.3.4), (A.3.7), (A.3.8), (A.3.9), (A.3.12), (A.3.14), (A.3.15), (A.3.16), (A.3.19), (A.3.20), (A.3.21), (A.3.22), (A.3.23), (A.3.24), (A.3.25), (A.3.26), (A.3.27); (A.4.5), (A.4.6), (A.4.8), (A.4.9), (A.4.11), (A.1.23), (A.1.24), (A.1.25), (A.1.26), (A.1.27), (A.1.28), (A.1.29), (A.1.30), (A.1.31), (A.1.32), and (A.1.33).

Preference is given to mixtures as component 2) at least one active substance selected from group B), which is particularly selected from (B.1.4), (B.1.5), diniconazole (B.1.6), (B.1.8), (B.1.10), (B.1.11), (B.1.12), (B.1.17), (B.1.18), (B.1.21), (B.1.22), (B.1.23), (B.1.25), (B.1.26), (B.1.27), (B.1.28), (B.1.29), uni (B.1.31), (B.1.32), (B.1.33), (B.1.34), (B.1.35), (B.1.36), (B.1.37), (B.1.38), (B.1.39), (B.1.40), (B.1.41), (B.1.42), (B.1.44), (B.1.46), (B.1.49) and (B.1.50; (B.2.2), (B.2.4), (B.2.5), (B.2.6), piperalin (B.2.7), (B.2.8); and (B.3.1).

Preference is given to mixtures comprising as component 2) at least one active substance selected from group C), which is particularly selected from (C.1.4), C.1.5), (C.1.6), and (C.2.4).

Preference is given to mixtures comprising as component 2) at least one active substance selected from group D), which is particularly selected from (D1.1), (D1.2), (D1.4), (D1.5); (D2.2), (D2.4), (D2.5), (D2.6) and (D2.7);

Preference is also given to mixtures comprising as component 2) at least one active substance selected from group E), which is particularly selected from (E.1.1), (E.1.2), and (E.1.3); Preference is also given to mixtures comprising as component 2) at least one active substance selected from group F), which is particularly selected from (F.1.2), (F.1.4), (F.1.5), (F.1.6) and (F.2.1).

Preference is also given to mixtures as component 2) at least one active substance selected from group G), which is particularly selected from (G.3.1), (G.3.2), (G.3.3), (G.3.4), (G.3.5), (G.3.6), (G.4.1) and (G.5.1).

Preference is also given to mixtures comprising as component 2) at least one active substance selected from group H), which is and particularly selected from (H.1.2), (H.1.3), copper oxychloride (H.1.4), (H.1.5), (H.1.6); (H.2.2), (H.2.5), (H.2.7), (H.3.2), (H.3.3), (H.3.4), (H.3.5), (H.3.6), (H.3.12); (H.4.2), (H.4.6), dithianon (H.4.9) and (H.4.10).

Preference is also given to mixtures comprising as component 2) at least one active substance selected from group I), which is particularly selected from (I.2.3) and (I.2.5).

Preference is also given to mixtures comprising as component 2) at least one active substance selected from group J), which is particularly selected from (J.1.1), (J.1.2), (J.1.3), (J.1.4), (J.1.6), (J.1.7), (J.1.8) and (J.1.9).

Preference is also given to mixtures comprising as component 2) at least one active substance selected from group K), which is particularly selected from (K.1.4), (K.1.5), (K.1.8), (K.1.12), (K.1.14), (K.1.15), (K.1.19) and (K.1.22).

Accordingly, the present invention furthermore relates to mixtures comprising one compound I (component 1) and one pesticide II (component 2), wherein pesticide II is selected from the column "Co. 2" of the lines B-1 to B-580 of Table B.

A further embodiment relates to the mixtures B-1 to B-580 listed in Table B, where a row of Table B corresponds in each case to a fungicidal mixture comprising as active components one of the in the present specification individualized compounds of formula I (component 1) and the respective pesticide II from groups A) to O) (component 2) stated in the row in question.

Another embodiment relates to the mixtures B-1 to B-580 listed in Table B, where a row of Table B corresponds in each case to a fungicidal mixture comprising as active components one of the compounds I-1 to I-288 of formula I as defined below in table 1 (component 1) and the respective pesticide II from groups A) to O) (component 2) stated in the row in question.

Preferably, the compositions described comprise the active components in synergistically effective amounts.

TABLE B

Mixtures comprising as active components one indiviualized compound of the fomula I (in column Co. 1), in particular compounds I-1 to I-289 as defined below in table I, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-1 | (I) | (A.1.1) |
| B-2 | (I) | (A.1.2) |
| B-3 | (I) | (A.1.3) |
| B-4 | (I) | (A.1.4) |
| B-5 | (I) | (A.1.5) |
| B-6 | (I) | (A.1.6) |
| B-7 | (I) | (A.1.7) |
| B-8 | (I) | (A.1.8) |
| B-9 | (I) | (A.1.9) |
| B-10 | (I) | (A.1.10) |
| B-11 | (I) | (A.1.11) |
| B-12 | (I) | (A.1.12) |
| B-13 | (I) | (A.1.13) |
| B-14 | (I) | (A.1.14) |
| B-15 | (I) | (A.1.15) |
| B-16 | (I) | (A.1.16) |
| B-17 | (I) | (A.1.17) |
| B-18 | (I) | (A.1.18) |

TABLE B-continued

Mixtures comprising as active components one indiviualized compound of the fomula I (in column Co. 1), in particular compounds I-1 to I-289 as defined below in table I, and as component 2) (in column Co. 2) one pesticide from groups A) to O) [which is coded e.g. as (A.1.1) for azoxystrobin as defined above].

| Mixt. | Co. 1 | Co. 2 |
| --- | --- | --- |
| B-19 | (I) | (A.1.19) |
| B-20 | (I) | (A.1.20) |
| B-21 | (I) | (A.1.21) |
| B-22 | (I) | (A.1.22) |
| B-23 | (I) | (A.1.23) |
| B-24 | (I) | (A.1.24) |
| B-25 | (I) | (A.1.25) |
| B-26 | (I) | (A.1.26) |
| B-27 | (I) | (A.1.27) |
| B-28 | (I) | (A.1.28) |
| B-29 | (I) | (A.1.29) |
| B-30 | (I) | (A.1.30) |
| B-31 | (I) | (A.1.31) |
| B-32 | (I) | (A.1.32) |
| B-33 | (I) | (A.1.33) |
| B-34 | (I) | (A.2.1) |
| B-35 | (I) | (A.2.2) |
| B-36 | (I) | (A.2.3) |
| B-37 | (I) | (A.2.4) |
| B-38 | (I) | (A.2.5) |
| B-39 | (I) | (A.2.6) |
| B-40 | (I) | (A.2.7) |
| B-41 | (I) | (A.2.8) |
| B-42 | (I) | (A.3.1) |
| B-43 | (I) | (A.3.2) |
| B-44 | (I) | (A.3.3) |
| B-45 | (I) | (A.3.4) |
| B-46 | (I) | (A.3.5) |
| B-47 | (I) | (A.3.6) |
| B-48 | (I) | (A.3.7) |
| B-49 | (I) | (A.3.8) |
| B-50 | (I) | (A.3.9) |
| B-51 | (I) | (A.3.10) |
| B-52 | (I) | (A.3.11) |
| B-53 | (I) | (A.3.12) |
| B-54 | (I) | (A.3.13) |
| B-55 | (I) | (A.3.14) |
| B-56 | (I) | (A.3.15) |
| B-57 | (I) | (A.3.16) |
| B-58 | (I) | (A.3.17) |
| B-59 | (I) | (A.3.18) |
| B-60 | (I) | (A.3.19) |
| B-61 | (I) | (A.3.20) |
| B-62 | (I) | (A.3.21) |
| B-63 | (I) | (A.3.22) |
| B-64 | (I) | (A.3.23) |
| B-65 | (I) | (A.3.24) |
| B-66 | (I) | (A.3.25) |
| B-67 | (I) | (A.3.26) |
| B-68 | (I) | (A.3.27) |
| B-69 | (I) | (A.4.1) |
| B-70 | (I) | (A.4.2) |
| B-71 | (I) | (A.4.3) |
| B-72 | (I) | (A.4.4) |
| B-73 | (I) | (A.4.5) |
| B-74 | (I) | (A.4.6) |
| B-75 | (I) | (A.4.7) |
| B-76 | (I) | (A.4.8) |
| B-77 | (I) | (A.4.9) |
| B-78 | (I) | (A.4.10) |
| B-79 | (I) | (A.4.11) |
| B-80 | (I) | (A.4.12) |
| B-81 | (I) | (B.1.1) |
| B-82 | (I) | (B.1.2) |
| B-83 | (I) | (B.1.3) |
| B-84 | (I) | (B.1.4) |
| B-85 | (I) | (B.1.5) |
| B-86 | (I) | (B.1.6) |
| B-87 | (I) | (B.1.7) |
| B-88 | (I) | (B.1.8) |
| B-89 | (I) | (B.1.9) |
| B-90 | (I) | (B.1.10) |
| B-91 | (I) | (B.1.11) |
| B-92 | (I) | (B.1.12) |
| B-93 | (I) | (B.1.13) |
| B-94 | (I) | (B.1.14) |
| B-95 | (I) | (B.1.15) |
| B-96 | (I) | (B.1.16) |
| B-97 | (I) | (B.1.17) |
| B-98 | (I) | (B.1.18) |
| B-99 | (I) | (B.1.19) |
| B-100 | (I) | (B.1.20) |
| B-101 | (I) | (B.1.21) |
| B-102 | (I) | (B.1.22) |
| B-103 | (I) | (B.1.23) |
| B-104 | (I) | (B.1.24) |
| B-105 | (I) | (B.1.25) |
| B-106 | (I) | (B.1.26) |
| B-107 | (I) | (B.1.27) |
| B-108 | (I) | (B.1.28) |
| B-109 | (I) | (B.1.29) |
| B-110 | (I) | (B.1.30) |
| B-111 | (I) | (B.1.31) |
| B-112 | (I) | (B.1.32) |
| B-113 | (I) | (B.1.33) |
| B-114 | (I) | (B.1.34) |
| B-115 | (I) | (B.1.35) |
| B-116 | (I) | (B.1.36) |
| B-117 | (I) | (B.1.37) |
| B-118 | (I) | (B.1.38) |
| B-119 | (I) | (B.1.39) |
| B-120 | (I) | (B.1.40) |
| B-121 | (I) | (B.1.41) |
| B-122 | (I) | (B.1.42) |
| B-123 | (I) | (B.1.43) |
| B-124 | (I) | (B.1.44) |
| B-125 | (I) | (B.1.45) |
| B-126 | (I) | (B.1.46) |
| B-127 | (I) | (B.1.47) |
| B-128 | (I) | (B.1.48) |
| B-129 | (I) | (B.1.49) |
| B-130 | (I) | (B.1.50) |
| B-131 | (I) | (B.1.51) |
| B-132 | (I) | (B.2.1) |
| B-133 | (I) | (B.2.2) |
| B-134 | (I) | (B.2.3) |
| B-135 | (I) | (B.2.4) |
| B-136 | (I) | (B.2.5) |
| B-137 | (I) | (B.2.6) |
| B-138 | (I) | (B.2.7) |
| B-139 | (I) | (B.2.8) |
| B-140 | (I) | (B.3.1) |
| B-141 | (I) | (C.1.1) |
| B-142 | (I) | (C.1.2) |
| B-143 | (I) | (C.1.3) |
| B-144 | (I) | (C.1.4) |
| B-145 | (I) | (C.1.5) |
| B-146 | (I) | (C.1.6) |
| B-147 | (I) | (C.1.7) |
| B-148 | (I) | (C.2.1) |
| B-149 | (I) | (C.2.2) |
| B-150 | (I) | (C.2.3) |
| B-151 | (I) | (C.2.4) |
| B-152 | (I) | (C.2.5) |
| B-153 | (I) | (C.2.6) |
| B-154 | (I) | (C.2.7) |
| B-155 | (I) | (D.1.1) |
| B-156 | (I) | (D.1.2) |
| B-157 | (I) | (D.1.3) |
| B-158 | (I) | (D.1.4) |
| B-159 | (I) | (D.1.5) |
| B-160 | (I) | (D.1.6) |
| B-161 | (I) | (D.2.1) |
| B-162 | (I) | (D.2.2) |

TABLE B-continued

Mixtures comprising as active components one indiviualized compound of the fomula I (in column Co. 1), in particular compounds I-1 to I-289 as defined below in table I, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-163 | (I) | (D.2.3) |
| B-164 | (I) | (D.2.4) |
| B-165 | (I) | (D.2.5) |
| B-166 | (I) | (D.2.6) |
| B-167 | (I) | (D.2.7) |
| B-168 | (I) | (E.1.1) |
| B-169 | (I) | (E.1.2) |
| B-170 | (I) | (E.1.3) |
| B-171 | (I) | (E.2.1) |
| B-172 | (I) | (E.2.2) |
| B-173 | (I) | (E.2.3) |
| B-174 | (I) | (E.2.4) |
| B-175 | (I) | (E.2.5) |
| B-176 | (I) | (E.2.6) |
| B-177 | (I) | (E.2.7) |
| B-178 | (I) | (E.2.8) |
| B-179 | (I) | (F.1.1) |
| B-180 | (I) | (F.1.2) |
| B-181 | (I) | (F.1.3) |
| B-182 | (I) | (F.1.4) |
| B-183 | (I) | (F.1.5) |
| B-184 | (I) | (F.1.6) |
| B-185 | (I) | (F.2.1) |
| B-186 | (I) | (G.1.1) |
| B-187 | (I) | (G.1.2) |
| B-188 | (I) | (G.1.3) |
| B-189 | (I) | (G.1.4) |
| B-190 | (I) | (G.2.1) |
| B-191 | (I) | (G.2.2) |
| B-192 | (I) | (G.2.3) |
| B-193 | (I) | (G.2.4) |
| B-194 | (I) | (G.2.5) |
| B-195 | (I) | (G.2.6) |
| B-196 | (I) | (G.2.7) |
| B-197 | (I) | (G.3.1) |
| B-198 | (I) | (G.3.2) |
| B-199 | (I) | (G.3.3) |
| B-200 | (I) | (G.3.4) |
| B-201 | (I) | (G.3.5) |
| B-202 | (I) | (G.3.6) |
| B-203 | (I) | (G.3.7) |
| B-204 | (I) | (G.3.8) |
| B-205 | (I) | (G.4.1) |
| B-206 | (I) | (G.5.1) |
| B-207 | (I) | (G.5.2) |
| B-208 | (I) | (G.5.3) |
| B-209 | (I) | (H.1.1) |
| B-210 | (I) | (H.1.2) |
| B-211 | (I) | (H.1.3) |
| B-212 | (I) | (H.1.4) |
| B-213 | (I) | (H.1.5) |
| B-214 | (I) | (H.1.6) |
| B-215 | (I) | (H.2.1) |
| B-216 | (I) | (H.2.2) |
| B-217 | (I) | (H.2.3) |
| B-218 | (I) | (H.2.4) |
| B-219 | (I) | (H.2.5) |
| B-220 | (I) | (H.2.6) |
| B-221 | (I) | (H.2.7) |
| B-222 | (I) | (H.2.8) |
| B-223 | (I) | (H.2.9) |
| B-224 | (I) | (H.3.1) |
| B-225 | (I) | (H.3.2) |
| B-226 | (I) | (H.3.3) |
| B-227 | (I) | (H.3.4) |
| B-228 | (I) | (H.3.5) |
| B-229 | (I) | (H.3.6) |
| B-230 | (I) | (H.3.7) |
| B-231 | (I) | (H.3.8) |
| B-232 | (I) | (H.3.9) |
| B-233 | (I) | (H.3.10) |
| B-234 | (I) | (H.3.11) |
| B-235 | (I) | (H.4.1) |
| B-236 | (I) | (H.4.2) |
| B-237 | (I) | (H.4.3) |
| B-238 | (I) | (H.4.4) |
| B-239 | (I) | (H.4.5) |
| B-240 | (I) | (H.4.6) |
| B-241 | (I) | (H.4.7) |
| B-242 | (I) | (H.4.8) |
| B-243 | (I) | (H.4.9) |
| B-244 | (I) | (H.4.10) |
| B-245 | (I) | (I.1.1) |
| B-246 | (I) | (I.1.2) |
| B-247 | (I) | (I.2.1) |
| B-248 | (I) | (I.2.2) |
| B-249 | (I) | (I.2.3) |
| B-250 | (I) | (I.2.4) |
| B-251 | (I) | (I.2.5) |
| B-252 | (I) | (J.1.1) |
| B-253 | (I) | (J.1.2) |
| B-254 | (I) | (J.1.3) |
| B-255 | (I) | (J.1.4) |
| B-256 | (I) | (J.1.5) |
| B-257 | (I) | (J.1.6) |
| B-258 | (I) | (J.1.7) |
| B-259 | (I) | (J.1.8) |
| B-260 | (I) | (J.1.9) |
| B-261 | (I) | (K.1.1) |
| B-262 | (I) | (K.1.2) |
| B-263 | (I) | (K.1.3) |
| B-264 | (I) | (K.1.4) |
| B-265 | (I) | (K.1.5) |
| B-266 | (I) | (K.1.6) |
| B-267 | (I) | (K.1.7) |
| B-268 | (I) | (K.1.8) |
| B-269 | (I) | (K.1.9) |
| B-270 | (I) | (K.1.10) |
| B-271 | (I) | (K.1.11) |
| B-272 | (I) | (K.1.12) |
| B-273 | (I) | (K.1.13) |
| B-274 | (I) | (K.1.14) |
| B-275 | (I) | (K.1.15) |
| B-276 | (I) | (K.1.16) |
| B-277 | (I) | (K.1.17) |
| B-278 | (I) | (K.1.18) |
| B-279 | (I) | (K.1.19) |
| B-280 | (I) | (K.1.20) |
| B-281 | (I) | (K.1.21) |
| B-282 | (I) | (K.1.22) |
| B-283 | (I) | (K.1.23) |
| B-284 | (I) | (K.1.24) |
| B-285 | (I) | (K.1.25) |
| B-286 | (I) | (K.1.26) |
| B-287 | (I) | (K.1.27) |
| B-288 | (I) | (K.1.28) |
| B-289 | (I) | (K.1.29) |
| B-290 | (I) | (K.1.30) |
| B-291 | (I) | (K.1.31) |
| B-292 | (I) | (K.1.32) |
| B-293 | (I) | (K.1.33) |
| B-294 | (I) | (K.1.34) |
| B-295 | (I) | (K.1.35) |
| B-296 | (I) | (K.1.36) |
| B-297 | (I) | (K.1.37) |
| B-298 | (I) | (K.1.38) |
| B-299 | (I) | (K.1.39) |
| B-300 | (I) | (K.1.40) |
| B-301 | (I) | (K.1.41) |
| B-302 | (I) | (K.1.42) |
| B-303 | (I) | (K.1.43) |
| B-304 | (I) | (K.1.44) |
| B-305 | (I) | (K.1.45) |
| B-306 | (I) | (K.1.46) |

TABLE B-continued

Mixtures comprising as active components one indiviualized compound of the fomula I (in column Co. 1), in particular compounds I-1 to I-289 as defined below in table I, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-307 | (I) | (K.1.47) |
| B-308 | (I) | (K.1.48) |
| B-309 | (I) | (M.1.1) |
| B-310 | (I) | (M.1.2) |
| B-311 | (I) | (M.1.3) |
| B-312 | (I) | (M.1.4) |
| B-313 | (I) | (M.1.5) |
| B-314 | (I) | (M.1.6) |
| B-315 | (I) | (M.1.7) |
| B-316 | (I) | (M.1.8) |
| B-317 | (I) | (M.1.9) |
| B-318 | (I) | (M.1.10) |
| B-319 | (I) | (M.1.11) |
| B-320 | (I) | (M.1.12) |
| B-321 | (I) | (M.1.13) |
| B-322 | (I) | (M.1.14) |
| B-323 | (I) | (M.1.15) |
| B-324 | (I) | (M.1.16) |
| B-325 | (I) | (M.1.17) |
| B-326 | (I) | (M.1.18) |
| B-327 | (I) | (M.1.19) |
| B-328 | (I) | (M.1.20) |
| B-329 | (I) | (M.1.21) |
| B-330 | (I) | (M.1.22) |
| B-331 | (I) | (M.1.23) |
| B-332 | (I) | (M.1.24) |
| B-333 | (I) | (M.1.25) |
| B-334 | (I) | (M.1.26) |
| B-335 | (I) | (M.1.27) |
| B-336 | (I) | (M.1.28) |
| B-337 | (I) | (M.1.29) |
| B-338 | (I) | (M.1.30) |
| B-339 | (I) | (M.1.31) |
| B-340 | (I) | (M.1.32) |
| B-341 | (I) | (M.1.33) |
| B-342 | (I) | (M.1.34) |
| B-343 | (I) | (M.1.35) |
| B-344 | (I) | (M.1.36) |
| B-345 | (I) | (M.1.37) |
| B-346 | (I) | (M.1.38) |
| B-347 | (I) | (M.1.39) |
| B-348 | (I) | (M.1.40) |
| B-349 | (I) | (M.1.41) |
| B-350 | (I) | (M.1.42) |
| B-351 | (I) | (M.1.43) |
| B-352 | (I) | (M.1.44) |
| B-353 | (I) | (M.1.45) |
| B-354 | (I) | (M.1.46) |
| B-355 | (I) | (M.1.47) |
| B-356 | (I) | (M.1.48) |
| B-357 | (I) | (M.1.49) |
| B-358 | (I) | (M.1.50) |
| B-359 | (I) | (N.1.1) |
| B-360 | (I) | (N.1.2) |
| B-361 | (I) | (N.1.3) |
| B-362 | (I) | (N.1.4) |
| B-363 | (I) | (N.1.5) |
| B-364 | (I) | (N.2.1) |
| B-365 | (I) | (N.2.2) |
| B-366 | (I) | (N.2.3) |
| B-367 | (I) | (N.3.1) |
| B-368 | (I) | (N.3.2) |
| B-369 | (I) | (N.3.3) |
| B-370 | (I) | (N.3.4) |
| B-371 | (I) | (N.4.1) |
| B-372 | (I) | (N.5.1) |
| B-373 | (I) | (N.6.1) |
| B-374 | (I) | (N.6.2) |
| B-375 | (I) | (N.6.3) |
| B-376 | (I) | (N.6.4) |
| B-377 | (I) | (N.6.5) |
| B-378 | (I) | (N.7.1) |
| B-379 | (I) | (N.7.2) |
| B-380 | (I) | (N.7.3) |
| B-381 | (I) | (N.8.1) |
| B-382 | (I) | (N.9.1) |
| B-383 | (I) | (N.10.1) |
| B-384 | (I) | (N.10.2) |
| B-385 | (I) | (N.10.3) |
| B-386 | (I) | (N.10.4) |
| B-387 | (I) | (N.10.5) |
| B-388 | (I) | (N.11.1) |
| B-389 | (I) | (N.12.1) |
| B-390 | (I) | (N.12.2) |
| B-391 | (I) | (N.12.3) |
| B-392 | (I) | (N.12.4) |
| B-393 | (I) | (N.13.1) |
| B-394 | (I) | (N.13.2) |
| B-395 | (I) | (N.13.3) |
| B-396 | (I) | (N.13.4) |
| B-397 | (I) | (N.13.5) |
| B-398 | (I) | (N.13.6) |
| B-399 | (I) | (N.13.7) |
| B-400 | (I) | (N.13.8) |
| B-401 | (I) | (N.13.9) |
| B-402 | (I) | (N.14.1) |
| B-403 | (I) | (N.14.2) |
| B-404 | (I) | (N.14.3) |
| B-405 | (I) | (N.15.1) |
| B-406 | (I) | (N.16.1) |
| B-407 | (I) | (N.16.2) |
| B-408 | (I) | (N.17.1) |
| B-409 | (I) | (N.17.2) |
| B-410 | (I) | (N.17.3) |
| B-411 | (I) | (N.17.4) |
| B-412 | (I) | (N.17.5) |
| B-413 | (I) | (N.17.6) |
| B-414 | (I) | (N.17.7) |
| B-415 | (I) | (N.17.8) |
| B-416 | (I) | (N.17.9) |
| B-417 | (I) | (N.17.10) |
| B-418 | (I) | (N.17.11) |
| B-419 | (I) | (N.17.12) |
| B-420 | (I) | (O.1.1) |
| B-421 | (I) | (O.1.2) |
| B-422 | (I) | (O.1.3) |
| B-423 | (I) | (O.1.4) |
| B-424 | (I) | (O.1.5) |
| B-425 | (I) | (O.1.6) |
| B-426 | (I) | (O.1.7) |
| B-427 | (I) | (O.1.8) |
| B-428 | (I) | (O.1.9) |
| B-429 | (I) | (O.1.10) |
| B-430 | (I) | (O.1.11) |
| B-431 | (I) | (O.1.12) |
| B-432 | (I) | (O.1.13) |
| B-433 | (I) | (O.1.14) |
| B-434 | (I) | (O.1.15) |
| B-435 | (I) | (O.1.16) |
| B-436 | (I) | (O.1.17) |
| B-437 | (I) | (O.1.18) |
| B-438 | (I) | (O.1.19) |
| B-439 | (I) | (O.1.20) |
| B-440 | (I) | (O.1.21) |
| B-441 | (I) | (O.1.22) |
| B-442 | (I) | (O.1.23) |
| B-443 | (I) | (O.1.24) |
| B-444 | (I) | (O.1.25) |
| B-445 | (I) | (O.1.26) |
| B-446 | (I) | (O.1.27) |
| B-447 | (I) | (O.1.28) |
| B-448 | (I) | (O.1.29) |
| B-449 | (I) | (O.1.30) |
| B-450 | (I) | (O.1.31) |

TABLE B-continued

Mixtures comprising as active components one indiviualized compound of the fomula I (in column Co. 1), in particular compounds I-1 to I-289 as defined below in table I, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-451 | (I) | (O.1.32) |
| B-452 | (I) | (O.1.33) |
| B-453 | (I) | (O.1.34) |
| B-454 | (I) | (O.1.35) |
| B-455 | (I) | (O.1.36) |
| B-456 | (I) | (O.1.37) |
| B-457 | (I) | (O.1.38) |
| B-458 | (I) | (O.2.1) |
| B-459 | (I) | (O.2.2) |
| B-460 | (I) | (O.2.3) |
| B-461 | (I) | (O.2.4) |
| B-462 | (I) | (O.2.5) |
| B-463 | (I) | (O.2.6) |
| B-464 | (I) | (O.2.7) |
| B-465 | (I) | (O.2.8) |
| B-466 | (I) | (O.2.9) |
| B-467 | (I) | (O.2.10) |
| B-468 | (I) | (O.2.11) |
| B-469 | (I) | (O.2.12) |
| B-470 | (I) | (O.2.13) |
| B-471 | (I) | (O.2.14) |
| B-472 | (I) | (O.2.15) |
| B-473 | (I) | (O.2.16) |
| B-474 | (I) | (O.3.1) |
| B-475 | (I) | (O.3.2) |
| B-476 | (I) | (O.3.3) |
| B-477 | (I) | (O.3.4) |
| B-478 | (I) | (O.3.5) |
| B-479 | (I) | (O.3.6) |
| B-480 | (I) | (O.3.7) |
| B-481 | (I) | (O.3.8) |
| B-482 | (I) | (O.3.9) |
| B-483 | (I) | (O.3.10) |
| B-484 | (I) | (O.3.11) |
| B-485 | (I) | (O.3.12) |
| B-486 | (I) | (O.3.13) |
| B-487 | (I) | (O.3.14) |
| B-488 | (I) | (O.3.15) |
| B-489 | (I) | (O.3.16) |
| B-490 | (I) | (O.3.17) |
| B-491 | (I) | (O.3.18) |
| B-492 | (I) | (O.3.19) |
| B-493 | (I) | (O.3.20) |
| B-494 | (I) | (O.3.21) |
| B-495 | (I) | (O.3.22) |
| B-496 | (I) | (O.3.23) |
| B-497 | (I) | (O.3.24) |
| B-498 | (I) | (O.3.25) |
| B-499 | (I) | (O.3.26) |
| B-500 | (I) | (O.3.27) |
| B-501 | (I) | (O.4.1) |
| B-502 | (I) | (O.4.2) |
| B-503 | (I) | (O.4.3) |
| B-504 | (I) | (O.4.4) |
| B-505 | (I) | (O.4.5) |
| B-506 | (I) | (O.4.6) |
| B-507 | (I) | (O.4.7) |
| B-508 | (I) | (O.4.8) |
| B-509 | (I) | (O.4.9) |
| B-510 | (I) | (O.4.10) |
| B-511 | (I) | (O.4.11) |
| B-512 | (I) | (O.4.12) |
| B-513 | (I) | (O.4.13) |
| B-514 | (I) | (O.4.14) |
| B-515 | (I) | (O.4.15) |
| B-516 | (I) | (O.4.16) |
| B-517 | (I) | (O.4.17) |
| B-518 | (I) | (O.4.18) |
| B-519 | (I) | (O.4.19) |
| B-520 | (I) | (O.4.20) |
| B-521 | (I) | (O.4.21) |
| B-522 | (I) | (O.4.22) |
| B-523 | (I) | (O.4.23) |
| B-524 | (I) | (O.4.24) |
| B-525 | (I) | (O.5.1) |
| B-526 | (I) | (O.5.2) |
| B-527 | (I) | (O.5.3) |
| B-528 | (I) | (O.5.4) |
| B-529 | (I) | (O.5.5) |
| B-530 | (I) | (O.5.6) |
| B-531 | (I) | (O.5.7) |
| B-532 | (I) | (O.5.8) |
| B-533 | (I) | (O.5.9) |
| B-534 | (I) | (O.6.1) |
| B-535 | (I) | (O.6.2) |
| B-536 | (I) | (O.6.3) |
| B-537 | (I) | (O.6.4) |
| B-538 | (I) | (O.6.5) |
| B-539 | (I) | (O.6.6) |
| B-540 | (I) | (O.6.7) |
| B-541 | (I) | (O.7.1) |
| B-542 | (I) | (O.7.2) |
| B-543 | (I) | (O.7.3) |
| B-544 | (I) | (O.7.4) |
| B-545 | (I) | (O.7.5) |
| B-546 | (I) | (O.7.6) |
| B-547 | (I) | (O.8.1) |
| B-548 | (I) | (O.8.2) |
| B-549 | (I) | (O.8.3) |
| B-550 | (I) | (O.8.4) |
| B-551 | (I) | (O.8.5) |
| B-552 | (I) | (O.9.1) |
| B-553 | (I) | (O.9.2) |
| B-554 | (I) | (O.9.3) |
| B-555 | (I) | (O.10.1) |
| B-556 | (I) | (O.11.1) |
| B-557 | (I) | (O.11.2) |
| B-558 | (I) | (O.11.3) |
| B-559 | (I) | (O.11.4) |
| B-560 | (I) | (O.12.1) |
| B-561 | (I) | (O.13.1) |
| B-562 | (I) | (O.14.1) |
| B-563 | (I) | (O.14.2) |
| B-564 | (I) | (O.15.1) |
| B-565 | (I) | (O.15.2) |
| B-566 | (I) | (O.15.3) |
| B-567 | (I) | (O.15.4) |
| B-568 | (I) | (O.15.5) |
| B-569 | (I) | (O.15.6) |
| B-570 | (I) | (O.15.7) |
| B-571 | (I) | (O.15.8) |
| B-572 | (I) | (O.15.9) |
| B-573 | (I) | (O.15.10) |
| B-574 | (I) | (O.15.11) |
| B-575 | (I) | (O.16.1) |
| B-576 | (I) | (O.16.2) |
| B-577 | (I) | (O.16.3) |
| B-578 | (I) | (O.16.4) |
| B-579 | (I) | (O.16.5) |
| B-580 | (I) | (O.16.6) |

The mixtures of active substances can be prepared as compositions comprising besides the active ingredients at least one inert ingredient (auxiliary) by usual means, e.g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is refereed to the explanations regarding the fungicidal activity of the compounds and the compositions containing compounds I, respectively.

I. SYNTHESIS EXAMPLES

The compounds of formula I can be prepared according to the methods outlined below and according to procedures that are set forth in WO 2013/008162 A1 and WO 2013/080120 A1.

Scheme 1

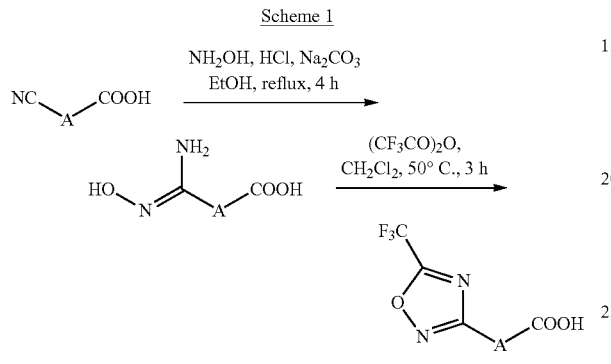

Step 1
General procedure for the preparation of N-hydroxylamidine: To a stirring solution of the appropriate nitrile (109.9 mmol) in ethanol (200 mL) was added solid sodium bicarbonate (7.6 g, 109.9 mmol), followed by hydroxylamine hydrochloride (10.1 g, 120.9 mmol). The reaction mixture was then heated to reflux (oil bath) for 4 h at which time it was cooled to room temperature. The reaction was quenched with water (400 mL) and the precipitate was collected by filtration, washed with water and diethyl ether:hexane (1:1). The solid was dried under reduced pressure to give the title compound.

Step 2
General procedure for the preparation of trifluoro-oxadiazoles: To a stirring solution of intermediate N-hydroxylamidine (4.65 mmol) in dichlormethane was added trifluoroacetic anhydride (10.2 mmol) and then the reaction was heated to 40° C. (oil bath). After 3 h the reaction was cooled to rt and concentrated under reduced pressure.

Purification of this material was accomplished by flash column chromatography eluting with 20% EtOAc/hexanes. The product containing fractions were collected and concentrated to give title compound.

Scheme 2

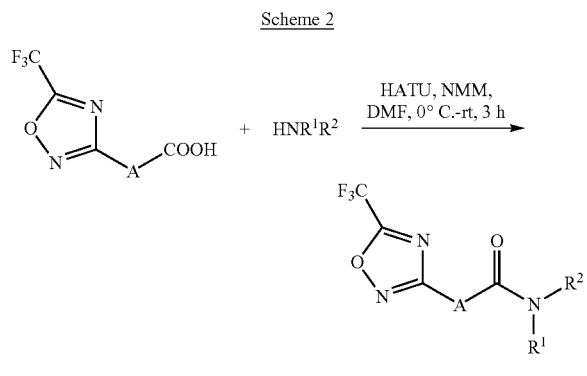

General procedure for the preparation of trifluoro-oxadiazole amides: To the appropriate trifluoro-oxadiazole carboxylic acid (0.155 mmol) in N,N-dimethylformamide (500 mL) were added 1-[Bis(dimethylamino)methylene]-1H-1,2,3-triazolo[4,5-b]pyridinium 3-oxid hexafluorophosphate (70.7 mg, 0.186 mmol) and N-methyl morpholine (34.1 mL, 0.310 mmol). The reaction was stirred for 30 min, the appropriate amine (0.186 mmol) added and then stirred for another hour. Purification of this material was accomplished by flash column chromatography eluting with 20% ethyl acetate/hexanes. Fractions containing the desired compound were combined and concentrated in vacuum to yield the final compound.

Scheme 3

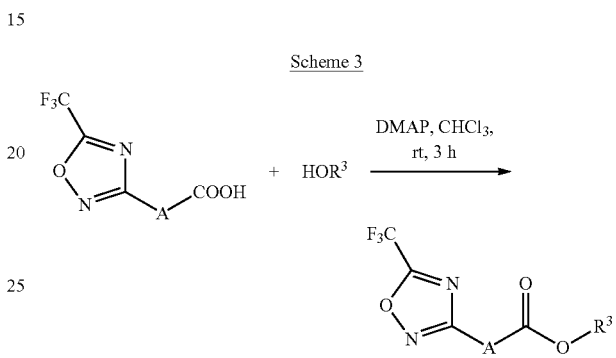

General procedure for the preparation of trifluoro-oxadiazole esters: To the appropriate trifluoro-oxadiazole (0.155 mmol) in trichloromethane (200 mL) was added 4-dimethylaminopyridine (22.7 mg, 0.186 mmol) and the appropriate alcohol (0.186 mmol). The reaction was stirred for 3 hours. Purification of this material was accomplished by flash column chromatography eluting with 20% ethyl acetate/hexanes. Fractions containing the desired compound were combined and concentrated in vacuum to yield the desired trifluoro-oxadiazole esters.

The compounds listed in Table I have been prepared in an analogous manner.

TABLE I

Compounds I-1 to I-289 of formula I, wherein Group A is selected in each case from one line of table A given below and the group W is selected in each case from one line of table W as given below.

| Ex. no | A | Y | W | HPLC R$_t$ (min)* |
|---|---|---|---|---|
| I-1 | A-1 | O | W-1 | 1.259 |
| I-2 | A-1 | O | W-2 | 1.301 |
| I-3 | A-1 | O | W-3 | 1.321 |
| I-4 | A-1 | O | W-4 | 1.360 |
| I-5 | A-1 | O | W-5 | 1.314 |
| I-6 | A-1 | O | W-6 | 1.331 |
| I-7 | A-1 | O | W-7 | 0.925 |
| I-8 | A-1 | O | W-8 | 1.223 |
| I-9 | A-1 | O | W-9 | 0.984 |
| I-10 | A-1 | O | W-10 | 1.323 |
| I-11 | A-1 | O | W-11 | 1.275 |
| I-12 | A-1 | O | W-12 | 1.327 |
| I-13 | A-1 | O | W-13 | 1.256 |
| I-14 | A-1 | O | W-14 | 1.349 |
| I-15 | A-1 | O | W-15 | 1.318 |
| I-16 | A-1 | O | W-16 | 1.255 |
| I-17 | A-1 | O | W-17 | 1.271 |
| I-18 | A-1 | O | W-18 | 1.436 |
| I-19 | A-1 | O | W-19 | 1.141 |
| I-20 | A-1 | O | W-20 | 1.198 |
| I-21 | A-1 | O | W-21 | 1.172 |

TABLE I-continued

Compounds I-1 to I-289 of formula I, wherein Group A is selected in each case from one line of table A given below and the group W is selected in each case from one line of table W as given below.

| Ex. no | A | Y | W | HPLC $R_t$ (min)* |
|---|---|---|---|---|
| I-22 | A-1 | O | W-22 | 1.172 |
| I-23 | A-1 | O | W-23 | 1.336 |
| I-24 | A-1 | O | W-24 | 0.999 |
| I-25 | A-1 | O | W-25 | 1.193 |
| I-26 | A-1 | O | W-26 | 1.164 |
| I-27 | A-1 | O | W-27 | 1.193 |
| I-28 | A-1 | O | W-28 | 1.230 |
| I-29 | A-1 | O | W-29 | 0.959 |
| I-30 | A-1 | O | W-30 | 0.886 |
| I-31 | A-1 | O | W-31 | 1.301 |
| I-32 | A-1 | O | W-32 | 1.246 |
| I-34 | A-1 | O | W-34 | 1.293 |
| I-35 | A-1 | O | W-35 | 1.388 |
| I-36 | A-1 | O | W-36 | 1.166 |
| I-37 | A-1 | O | W-37 | 1.380 |
| I-38 | A-1 | O | W-38 | 1.386 |
| I-39 | A-1 | O | W-39 | 1.345 |
| I-40 | A-1 | O | W-40 | 1.337 |
| I-41 | A-1 | O | W-41 | 1.370 |
| I-44 | A-1 | O | W-44 | 1.392 |
| I-45 | A-1 | O | W-45 | 1.161 |
| I-46 | A-1 | O | W-46 | 1.172 |
| I-47 | A-1 | O | W-47 | 1.317 |
| I-48 | A-1 | O | W-48 | 1.171 |
| I-49 | A-1 | O | W-49 | 1.189 |
| I-50 | A-1 | O | W-50 | 1.335 |
| I-51 | A-1 | O | W-51 | 1.334 |
| I-52 | A-1 | O | W-52 | 1.084 |
| I-53 | A-1 | O | W-53 | 1.100 |
| I-54 | A-1 | O | W-54 | 1.271 |
| I-55 | A-1 | O | W-55 | 1.071 |
| I-56 | A-1 | O | W-56 | 1.139 |
| I-57 | A-1 | O | W-57 | 1.008 |
| I-58 | A-1 | O | W-58 | 1.313 |
| I-59 | A-1 | O | W-59 | 1.347 |
| I-60 | A-1 | O | W-60 | 1.346 |
| I-61 | A-1 | O | W-61 | 1.325 |
| I-62 | A-1 | O | W-62 | 1.178 |
| I-63 | A-1 | O | W-63 | 1.396 |
| I-64 | A-1 | O | W-64 | 1.311 |
| I-65 | A-1 | O | W-65 | 1.334 |
| I-66 | A-1 | O | W-66 | 1.218 |
| I-67 | A-1 | O | W-67 | 1.154 |
| I-68 | A-2 | O | W-1 | 1.259 |
| I-69 | A-2 | O | W-2 | 1.317 |
| I-70 | A-2 | O | W-3 | 1.321 |
| I-71 | A-2 | O | W-5 | 1.300 |
| I-72 | A-3 | O | W-1 | 1.265 |
| I-73 | A-3 | O | W-2 | 1.318 |
| I-74 | A-4 | O | W-1 | 1.228 |
| I-75 | A-4 | O | W-2 | 1.325 |
| I-76 | A-5 | O | W-1 | 1.135 |
| I-77 | A-5 | O | W-2 | 1.172 |
| I-78 | A-6 | O | W-1 | 1.316 |
| I-79 | A-6 | O | W-2 | 1.367 |
| I-80 | A-7 | O | W-1 | 1.147 |
| I-81 | A-7 | O | W-2 | 1.181 |
| I-82 | A-8 | O | W-24 | 0.923 |
| I-83 | A-8 | O | W-79 | 1.006 |
| I-84 | A-8 | O | W-166 | 0.972 |
| I-85 | A-1 | O | W-68 | 1.308 |
| I-86 | A-1 | O | W-69 | 1.098 |
| I-87 | A-1 | O | W-70 | 1.339 |
| I-88 | A-1 | O | W-71 | 1.332 |
| I-89 | A-1 | O | W-72 | 1.414 |
| I-90 | A-1 | O | W-73 | 1.251 & 1.266 |
| I-91 | A-1 | O | W-74 | 1.170 |
| I-92 | A-1 | O | W-75 | 1.072 |
| I-94 | A-1 | O | W-77 | 1.170 |
| I-95 | A-1 | O | W-78 | 1.205 |
| I-96 | A-1 | O | W-79 | 1.137 |
| I-97 | A-1 | O | W-80 | 1.088 |
| I-98 | A-1 | O | W-81 | 1.116 |
| I-99 | A-1 | O | W-82 | 1.297 |
| I-100 | A-1 | O | W-83 | 1.366 |
| I-101 | A-1 | O | W-84 | 0.878 |
| I-102 | A-1 | O | W-85 | 1.263 |
| I-103 | A-1 | O | W-86 | 1.263 |
| I-105 | A-1 | O | W-88 | 1.258 |
| I-106 | A-1 | O | W-89 | 1.282 |
| I-107 | A-1 | O | W-90 | 1.126 |
| I-108 | A-1 | O | W-91 | 1.419 |
| I-109 | A-1 | O | W-92 | 1.213 |
| I-111 | A-1 | O | W-94 | 1.079 |
| I-112 | A-1 | O | W-95 | 1.128 |
| I-113 | A-1 | O | W-96 | 1.057 |
| I-114 | A-1 | O | W-97 | 1.069 |
| I-115 | A-1 | O | W-98 | 1.354 |
| I-116 | A-1 | O | W-99 | 1.282 |
| I-117 | A-1 | O | W-100 | 1.200 |
| I-118 | A-1 | O | W-101 | 1.008 |
| I-119 | A-1 | O | W-102 | 1.201 & 1.224 |
| I-120 | A-1 | O | W-103 | 0.983 |
| I-122 | A-1 | O | W-105 | 1.189 |
| I-124 | A-1 | O | W-107 | 1.121 |
| I-126 | A-1 | O | W-109 | 1.270 |
| I-128 | A-1 | O | W-111 | 1.163 |
| I-129 | A-1 | O | W-112 | 0.972 |
| I-130 | A-1 | O | W-113 | 1.062 |
| I-131 | A-1 | O | W-114 | 1.092 |
| I-132 | A-1 | O | W-115 | 0.969 |
| I-133 | A-1 | O | W-116 | 1.183 |
| I-134 | A-1 | O | W-117 | 0.996 |
| I-135 | A-1 | O | W-118 | 0.887 |
| I-136 | A-1 | O | W-119 | 0.821 |
| I-137 | A-1 | O | W-120 | 1.239 |
| I-140 | A-1 | O | W-123 | 1.285 |
| I-141 | A-1 | O | W-124 | 0.825 |
| I-143 | A-1 | O | W-126 | 1.240 |
| I-144 | A-1 | O | W-127 | 1.004 |
| I-145 | A-1 | O | W-128 | 1.234 |
| I-146 | A-1 | O | W-129 | 1.273 |
| I-147 | A-1 | O | W-130 | 1.227 |
| I-148 | A-1 | O | W-131 | 1.090 |
| I-149 | A-1 | O | W-132 | 1.098 |
| I-150 | A-1 | O | W-133 | 0.914 |
| I-152 | A-1 | O | W-135 | 1.127 |
| I-153 | A-1 | O | W-136 | 1.272 |
| I-154 | A-1 | O | W-137 | 1.204 |
| I-155 | A-1 | O | W-138 | 1.166 |
| I-156 | A-1 | O | W-139 | 1.284 |
| I-157 | A-1 | O | W-140 | 1.198 |
| I-158 | A-1 | O | W-141 | 1.151 |
| I-159 | A-1 | O | W-142 | 1.243 |
| I-160 | A-1 | O | W-143 | 1.115 |
| I-161 | A-1 | O | W-144 | 1.093 |
| I-162 | A-1 | O | W-145 | 0.917 |
| I-163 | A-1 | O | W-146 | 1.018 |
| I-165 | A-1 | O | W-148 | 1.143 |
| I-168 | A-1 | O | W-151 | 1.235 |
| I-169 | A-1 | O | W-152 | 1.240 |
| I-170 | A-1 | O | W-153 | 1.066 |
| I-171 | A-1 | O | W-154 | 1.208 |
| I-172 | A-1 | O | W-155 | 1.113 |
| I-173 | A-1 | O | W-156 | 1.142 |
| I-174 | A-1 | O | W-157 | 1.102 |
| I-175 | A-1 | O | W-158 | 1.115 |
| I-176 | A-1 | O | W-159 | 1.125 |
| I-178 | A-1 | O | W-161 | 1.259 |
| I-180 | A-1 | O | W-163 | 1.242 |
| I-182 | A-1 | O | W-165 | 1.195 |
| I-183 | A-1 | O | W-166 | 1.332 |
| I-184 | A-1 | O | W-167 | 1.330 |
| I-185 | A-1 | O | W-168 | 1.272 |
| I-186 | A-1 | O | W-169 | 1.201 |
| I-187 | A-1 | O | W-170 | 1.013 |

TABLE I-continued

Compounds I-1 to I-289 of formula I, wherein Group A is selected in each case from one line of table A given below and the group W is selected in each case from one line of table W as given below.

| Ex. no | A | Y | W | HPLC R_t (min)* |
|---|---|---|---|---|
| I-189 | A-1 | O | W-172 | 1.194 |
| I-190 | A-1 | O | W-173 | 1.115 |
| I-191 | A-1 | O | W-174 | 1.177 |
| I-192 | A-1 | O | W-175 | 1.209 |
| I-193 | A-1 | O | W-176 | 1.046 |
| I-194 | A-1 | O | W-177 | 1.268 |
| I-196 | A-1 | O | W-179 | 1.108 |
| I-198 | A-1 | O | W-181 | 1.260 |
| I-199 | A-1 | O | W-182 | 1.148 & 1.189 |
| I-200 | A-1 | O | W-183 | 1.067 |
| I-201 | A-1 | O | W-184 | 1.369 |
| I-202 | A-1 | O | W-185 | 1.013 |
| I-203 | A-1 | O | W-186 | 1.116 |
| I-205 | A-1 | O | W-188 | 1.365 |
| I-207 | A-1 | O | W-190 | 1.266 |
| I-208 | A-1 | O | W-191 | 1.128 |
| I-210 | A-1 | O | W-193 | 1.297 |
| I-211 | A-1 | O | W-194 | 1.315 |
| I-212 | A-1 | O | W-195 | 1.393 |
| I-213 | A-1 | O | W-196 | 1.267 |
| I-214 | A-1 | O | W-197 | 1.353 |
| I-215 | A-1 | O | W-198 | 1.256 |
| I-216 | A-1 | O | W-199 | 1.259 |
| I-217 | A-1 | O | W-200 | 1.335 |
| I-218 | A-1 | O | W-201 | 1.061 |
| I-219 | A-1 | O | W-202 | 0.886 |
| I-220 | A-1 | O | W-203 | 1.085 |
| I-222 | A-1 | O | W-205 | 1.176 |
| I-223 | A-1 | O | W-206 | 1.261 |
| I-224 | A-1 | O | W-207 | 1.278 |
| I-225 | A-1 | O | W-208 | 1.183 |
| I-226 | A-1 | O | W-209 | 1.265 |
| I-227 | A-1 | O | W-210 | 1.001 |
| I-228 | A-1 | O | W-211 | 1.098 |
| I-229 | A-1 | O | W-212 | 1.211 |
| I-230 | A-1 | O | W-213 | 1.298 |
| I-231 | A-1 | O | W-214 | 1.213 |
| I-232 | A-1 | O | W-215 | 1.107 |
| I-233 | A-1 | O | W-216 | 1.263 |
| I-235 | A-1 | O | W-218 | 1.081 |
| I-236 | A-1 | O | W-219 | 1.182 |
| I-237 | A-1 | O | W-220 | 1.213 |
| I-238 | A-1 | O | W-221 | 1.341 |
| I-240 | A-1 | O | W-223 | 1.119 |
| I-241 | A-1 | O | W-224 | 1.098 |
| I-242 | A-1 | O | W-225 | 1.219 |
| I-243 | A-1 | O | W-226 | 1.038 |
| I-244 | A-1 | O | W-227 | 1.109 |
| I-245 | A-1 | O | W-228 | 1.231 |
| I-246 | A-1 | O | W-229 | 1.085 |
| I-247 | A-1 | O | W-230 | 1.231 |
| I-248 | A-1 | O | W-231 | 1.205 |
| I-249 | A-1 | O | W-232 | 1.108 |
| I-250 | A-1 | O | W-233 | 1.362 |
| I-254 | A-1 | O | W-237 | 1.206 |
| I-255 | A-1 | O | W-238 | 1.226 |
| I-256 | A-1 | O | W-239 | 1.245 |
| I-257 | A-1 | O | W-240 | 1.282 |
| I-259 | A-1 | O | W-242 | 1.251 |
| I-260 | A-1 | O | W-243 | 1.320 |
| I-261 | A-1 | O | W-244 | 1.213 |
| I-263 | A-1 | O | W-246 | 1.107 |
| I-277 | A-1 | O | W-260 | 1.208 |
| I-283 | A-1 | O | W-266 | 1.318 |
| I-284 | A-1 | O | W-267 | 1.046 |
| I-286 | A-1 | O | W-269 | 1.223 |
| I-287 | A-1 | O | W-270 | 1.240 |
| I-288 | A-1 | O | W-271 | 1.190 |
| I-289 | A-1 | O | W-272 | 1.219 |

*HPLC: High Performance Liquid Chromatography; HPLC-column Kinetex XB C18 1.7μ (50 × 2.1 mm); eluent: acetonitrile/water + 0.1% trifluoroacetic acid (gradient from 5:95 to 100:0 in 1.5 min at 60° C., flow gradient from 0.8 to 1.0 ml/min in 1.5 min).
MS: Quadrupol Electrospray Ionisation, 80 V (positive mode).
R_t: retention time in minutes.

Group A in table 1 is to be construed as one of the following radicals A-1 to A-7 in table A, in which #1 indicates the point of attachment of the trifluorooxadiazole group and #2 indicates the point of attachment of the group —C(=Y)W.

TABLE A

| No. | |
|---|---|
| A-1 | 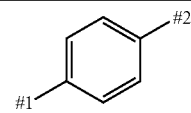 |
| A-2 | 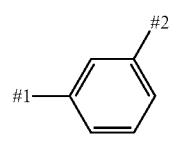 |
| A-3 | 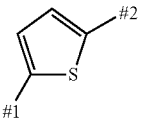 |
| A-4 | 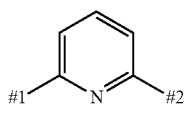 |
| A-5 | 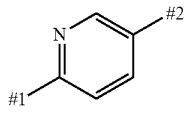 |
| A-6 | 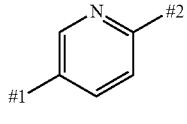 |
| A-7 | 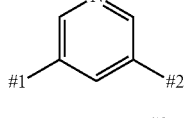 |
| A-8 | 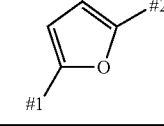 |

Group W in table 1 is to be construed as one of the following radicals W-1 to W-271 in table W. in which #3 indicates the point of attachment of the group A-C(=Y).

TABLE W

| No. | |
|---|---|
| W-1 | *2-anilino (NH-Ph), #3 on N* |
| W-2 | *2-methoxyanilino*, #3 on N |
| W-3 | *2-methoxy-4-fluoroanilino*, #3 on N |
| W-4 | *2-(trifluoromethoxy)anilino*, #3 on N |
| W-5 | *2-(difluoromethoxy)anilino*, #3 on N |
| W-6 | *2-chloroanilino*, #3 on N |
| W-7 | *3-methoxy-2-pyridylamino*, #3 on N |
| W-8 | *2-hydroxy-5-methylanilino*, #3 on N |
| W-9 | *4,5-dihydrothiazol-2-ylamino*, #3 on N |

TABLE W-continued

| No. | |
|---|---|
| W-10 | *N-ethyl-N-(2-phenylethyl)amino*, #3 on N |
| W-11 | *N-methyl-N-((3-methylthiophen-2-yl)methyl)amino*, #3 on N |
| W-12 | *(2-chloropyridin-3-yl)methoxy*, #3 on O-CH2 |
| W-13 | *1,4-oxazepan-4-yl*, #3 on N |
| W-14 | *2-fluoroanilino*, #3 on N |
| W-15 | *2-(difluoromethoxy)-4-fluoroanilino*, #3 on N |
| W-16 | *2-methoxy-6-(trifluoromethyl)anilino*, #3 on N |
| W-17 | *2-bromo-6-methylpyridin-3-ylamino*, #3 on N |
| W-18 | *2-(methoxycarbonyl)pyridin-3-ylamino*, #3 on N |

TABLE W-continued
| No. | |
|---|---|
| W-19 | 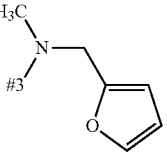 |
| W-20 | 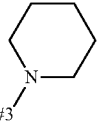 |
| W-21 | 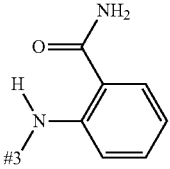 |
| W-22 | 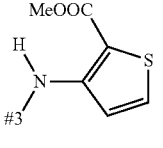 |
| W-23 | 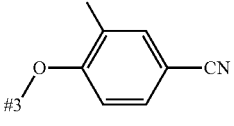 |
| W-24 |  |
| W-25 | 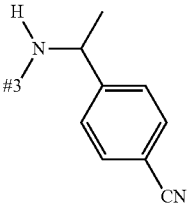 |
| W-26 | 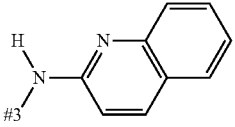 |
| W-27 | 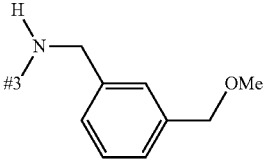 |
| W-28 | 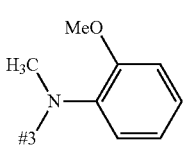 |
| W-29 | 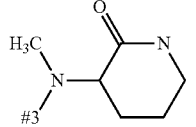 |
| W-30 | 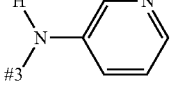 |
| W-31 | 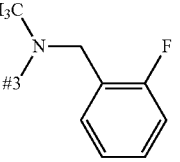 |
| W-32 | 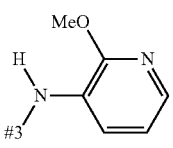 |
| W-34 | 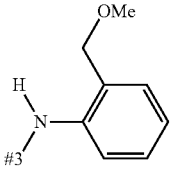 |
| W-35 | 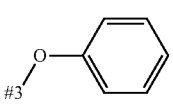 |
| W-36 | 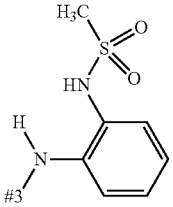 |
| W-37 | 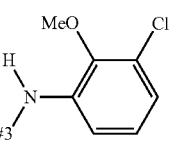 |
| W-38 | 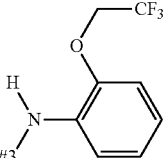 |
| W-39 | 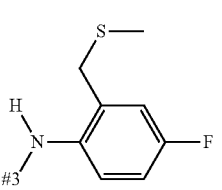 |

TABLE W-continued
| No. | |
|---|---|
| W-40 | 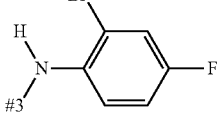 |
| W-41 | 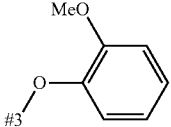 |
| W-44 | 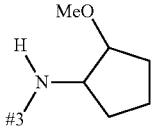 |
| W-45 | 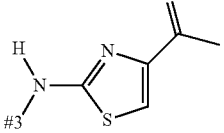 |
| W-46 | 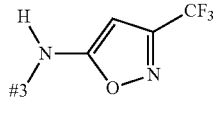 |
| W-47 | 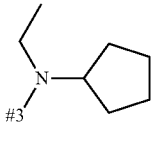 |
| W-48 | 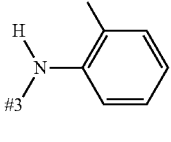 |
| W-49 | 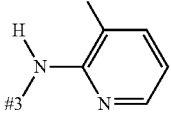 |
| W-50 | 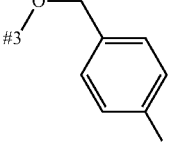 |
| W-51 | 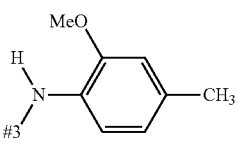 |
| W-52 | 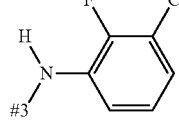 |
| W-53 | 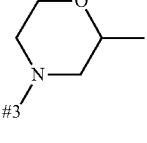 |
| W-54 | 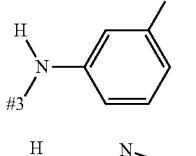 |
| W-55 | 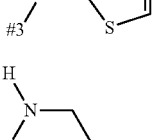 |
| W-56 | 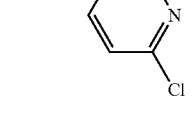 |
| W-57 | 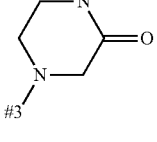 |
| W-58 | 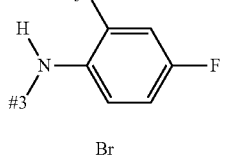 |
| W-59 | 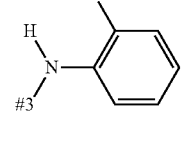 |
| W-60 | 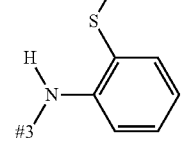 |
| W-61 | 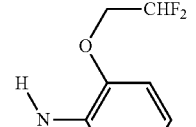 |

TABLE W-continued

| No. | |
|---|---|
| W-62 | 2,6-dimethoxyphenyl-NH-#3 |
| W-63 | 2-acetylphenyl-NH-#3 |
| W-64 | 3,5-difluorophenyl-NH-#3 |
| W-65 | #3-O-CH2-(furan-3-yl) |
| W-66 | #3-N(piperidine-2-COOMe) |
| W-67 | #3-O-CH2-(6-methoxypyridin-2-yl) |
| W-68 | #3-N(Et)(CH2-thiophen-2-yl) |
| W-69 | #3-N(piperazine-N'-CO-iPr) |
| W-70 | #3-N(Et)(cyclopropyl) |
| W-71 | #3-N(cyclopropyl)(CH2-thiophen-2-yl) |
| W-72 | #3-N(decahydroquinoline) |
| W-73 | #3-NH-(2,2,4,4-tetramethyl-3-methoxycyclobutyl) |
| W-74 | #3-NH-(thieno[3,2-d]pyrimidin-4-yl) |
| W-75 | #3-NH-(tetrahydropyran-4-yl) |
| W-77 | #3-CH2-(6-methoxypyridin-4-yl)-NH |
| W-78 | #3-CH2-(thiophen-2-yl)-NH |
| W-79 | #3-N(Et)(Me) |
| W-80 | #3-NH-cyclopropyl |
| W-81 | #3-NH-CH2-CH=CH2 |

TABLE W-continued
| No. | |
|---|---|
| W-82 | 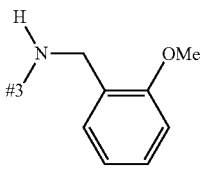 |
| W-83 | 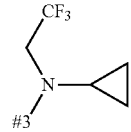 |
| W-84 | 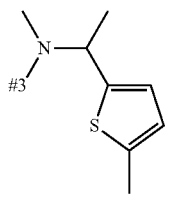 |
| W-85 | 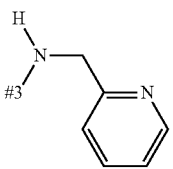 |
| W-86 | 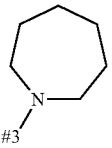 |
| W-88 | 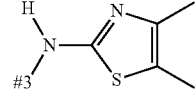 |
| W-89 | 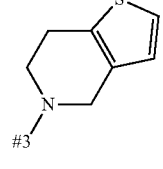 |
| W-90 | 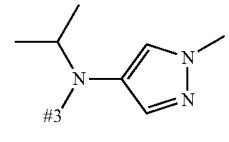 |
| W-91 | 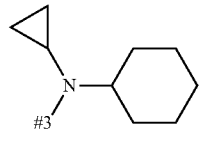 |
| W-92 | 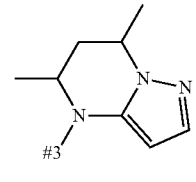 |
| W-94 | 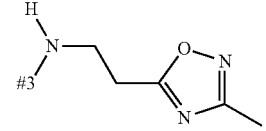 |
| W-95 | 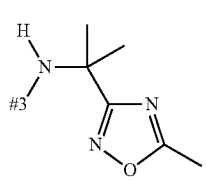 |
| W-96 | 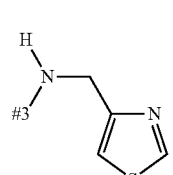 |
| W-97 | 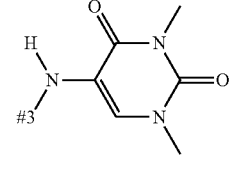 |
| W-98 | 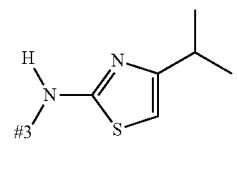 |
| W-99 | 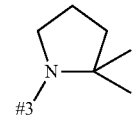 |
| W-100 | 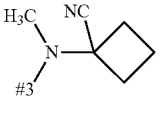 |
| W-101 | 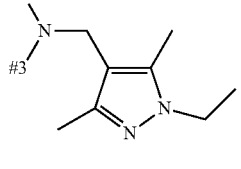 |
| W-102 | 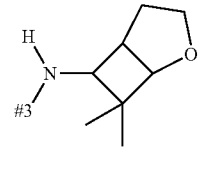 |

TABLE W-continued
| No. | |
|---|---|
| W-103 | 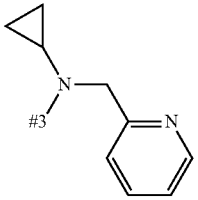 |
| W-105 | 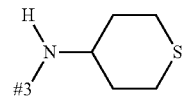 |
| W-107 | 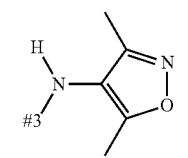 |
| W-109 | 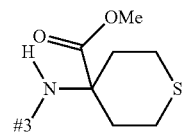 |
| W-111 | 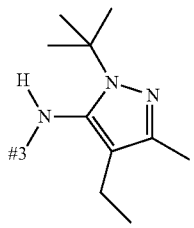 |
| W-112 | 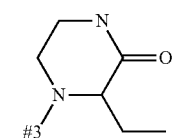 |
| W-113 | 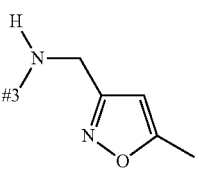 |
| W-114 | 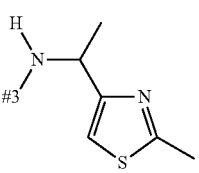 |
| W-115 | 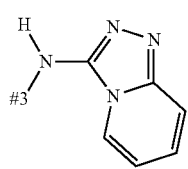 |
| W-116 | 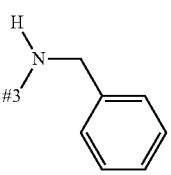 |
| W-117 | 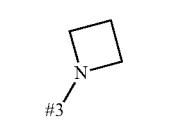 |
| W-118 | 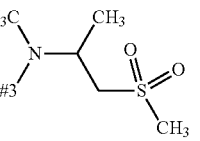 |
| W-119 | 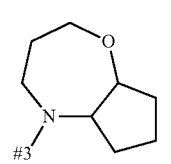 |
| W-120 | 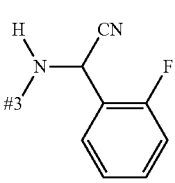 |
| W-123 | 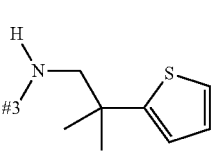 |
| W-124 | 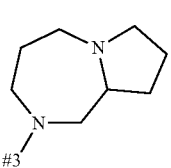 |
| W-126 | 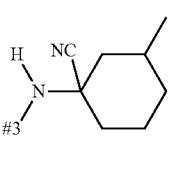 |
| W-127 | 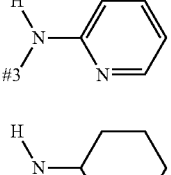 |
| W-128 | 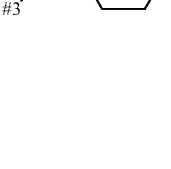 |

TABLE W-continued

| No. | Structure |
|---|---|
| W-129 | H₃C-N(#3)-CH(CH₃)-phenyl |
| W-130 | H₃C-N(#3)-CH₂-(3-methoxyphenyl) |
| W-131 | H₃C-N(#3)-(pyridin-2-yl) |
| W-132 | H₃C-N(#3)-(6-methylpyridin-2-yl) |
| W-133 | H-N(#3)-(3-hydroxypyridin-2-yl) |
| W-135 | H-N(#3)-(3-cyanotetrahydrothiophen-3-yl) |
| W-136 | H₃C-N(#3)-CH₂-phenyl |
| W-137 | H₃C-N(#3)-phenyl |
| W-138 | H₃C-N(#3)-CH₂-(furan-2-yl) |
| W-139 | H₃C-N(#3)-cyclohexyl |
| W-140 | H-N(#3)-(3-cyanophenyl) |
| W-141 | H-N(#3)-CH₂CH₂-(3-isopropyl-1,2,4-oxadiazol-5-yl) |
| W-142 | H-N(#3)-(3-chloro-2-hydroxyphenyl) |
| W-143 | H-N(#3)-CH₂-C(CH₃)(OH)-(5-methylfuran-2-yl) |
| W-144 | H-N(#3)-CH₂-CH(OH)-(3-fluorophenyl) |
| W-145 | H-N(#3)-CH₂-CH(OH)-(1-methylpyrazol-4-yl) |
| W-146 | morpholin-4-yl (#3) |
| W-148 | NC-CH₂CH₂-N(#3)-CH₂-(furan-2-yl) |
| W-151 | H-N(#3)-(4-chloro-2-hydroxyphenyl) |
| W-152 | H-N(#3)-(2,4-dimethoxyphenyl) |
| W-153 | 3-cyanomorpholin-4-yl (#3) |

TABLE W-continued
| No. | |
|---|---|
| W-154 | 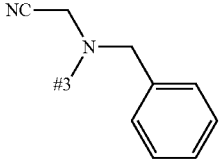 |
| W-155 | 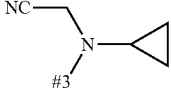 |
| W-156 | 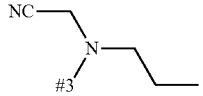 |
| W-157 | 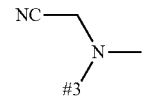 |
| W-158 | 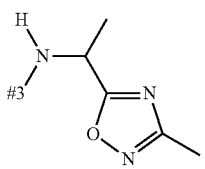 |
| W-159 | 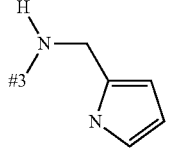 |
| W-161 | 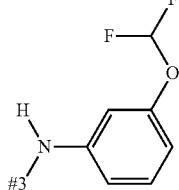 |
| W-162 | 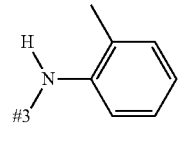 |
| W-163 | 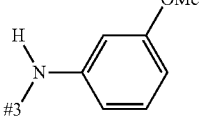 |
| W-165 | 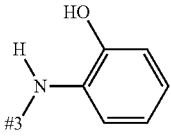 |
| W-166 | 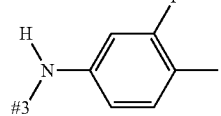 |
| W-167 | 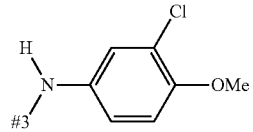 |
| W-168 | 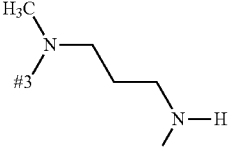 |
| W-169 | 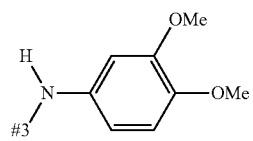 |
| W-170 | 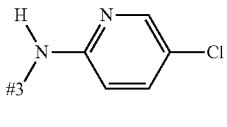 |
| W-171 | 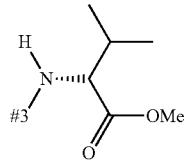 |
| W-172 | 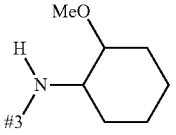 |
| W-173 | 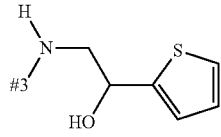 |
| W-174 | 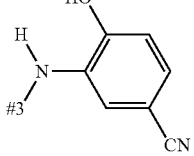 |
| W-175 | 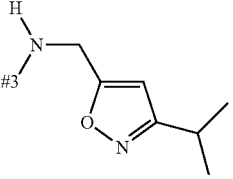 |

TABLE W-continued

| No. | Structure |
|---|---|
| W-176 | 4-(methylamino)-5-methoxy-1,3-dimethylpyrazole substituent (#3-NH-) |
| W-177 | #3-NH-C(CH₃)(CH₂CH₂CH₃)-C(=O)-OMe |
| W-179 | #3-NH-CH(CH₃)-C(=O)-OMe (stereo) |
| W-181 | #3-N(CH₂CF₃)(CH₂CH₂OMe) |
| W-182 | 2,6-dimethylmorpholin-4-yl (#3-N) |
| W-183 | #3-NH-CH₂-(3-methyl-1,2,4-oxadiazol-5-yl) |
| W-184 | #3-NH-(2-methoxy-5-chlorophenyl) |
| W-185 | 3-hydroxypiperidin-1-yl (#3-N) |
| W-186 | 3-hydroxy-3-(trifluoromethyl)pyrrolidin-1-yl (#3-N) |

TABLE W-continued

| No. | Structure |
|---|---|
| W-188 | #3-NH-CH₂-(4-dimethylaminophenyl) |
| W-190 | #3-N(cyclopentyl)(CH₂CH₂OMe) |
| W-191 | #3-N(Et)(CH₂CN) |
| W-193 | #3-NH-(4-methylphenyl) |
| W-194 | #3-NH-(2-chloro-4-methylphenyl) |
| W-195 | #3-NH-(quinolin-8-yl) |
| W-196 | #3-NH-(2-chloro-5-fluorophenyl) |
| W-197 | #3-N(cyclopropyl)-CH(CH₃)-(furan-2-yl) |
| W-198 | #3-NH-(2-chloro-4-methoxyphenyl) |

TABLE W-continued

| No. | |
|---|---|
| W-199 | [structure: 2,3-dihydro-1,4-benzodioxin-5-yl-NH-#3] |
| W-200 | [structure: thiazol-2-yl-CH2-NH-#3] |
| W-201 | [structure: 6-methylpyridin-2-yl-NH-#3] |
| W-202 | [structure: 1-methyl-4-cyano-piperidin-4-yl-NH-#3] |
| W-203 | [structure: 2-cyanomorpholin-4-yl, #3 on N] |
| W-205 | [structure: CH(CN)(thiophen-3-yl)-NH-#3] |
| W-206 | [structure: 2-chloro-4-fluorophenyl-NH-#3] |
| W-207 | [structure: 4-chloro-2-methylphenyl-NH-#3] |
| W-208 | [structure: 2-cyano-3-fluorophenyl-NH-#3] |
| W-209 | [structure: 4-methoxypyridin-3-yl-NH-#3] |
| W-210 | [structure: 1-methyl-2-oxo-1,2-dihydropyrazin-3-yl-NH-#3] |
| W-211 | [structure: HC≡C-CH2-NH-#3] |
| W-212 | [structure: 2-methoxybenzyl-NH-#3] |
| W-213 | [structure: 4-methoxyphenyl-NH-#3] |
| W-214 | [structure: 4-cyanophenyl-NH-#3] |
| W-215 | [structure: NC-CH2-NH-#3] |
| W-216 | [structure: cyclopropyl-CH2-NH-#3] |
| W-218 | [structure: 1-cyanocyclopropyl-NH-#3] |
| W-219 | [structure: MeO-C(O)-CH2-NH-#3] |
| W-220 | [structure: 5-methylisoxazol-3-yl-CH2-N(CH3)-#3] |
| W-221 | [structure: 1-(thiazol-2-yl)ethyl-NH-#3] |

TABLE W-continued
| No. | |
|---|---|
| W-223 | 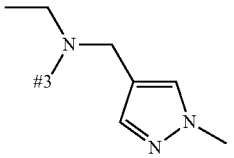 |
| W-224 | 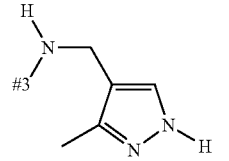 |
| W-225 | 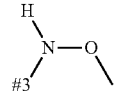 |
| W-226 | 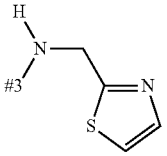 |
| W-227 | 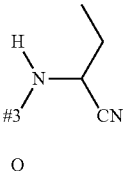 |
| W-228 | 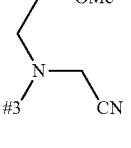 |
| W-229 | 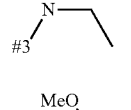 |
| W-230 | 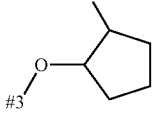 |
| W-231 | 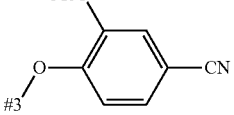 |
| W-232 | 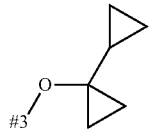 |
| W-233 | 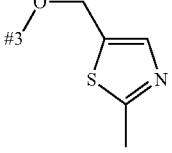 |
| W-237 | 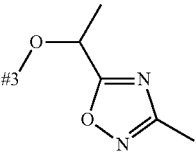 |
| W-238 | 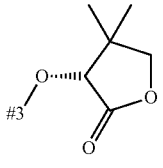 |
| W-239 | 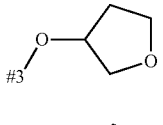 |
| W-240 | 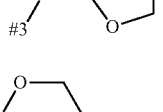 |
| W-242 | 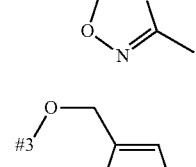 |
| W-243 | 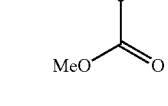 |
| W-244 | 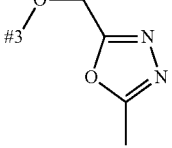 |
| W-246 | 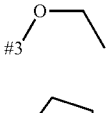 |
| W-260 | 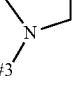 |

TABLE W-continued

| No. | |
|---|---|
| W-266 | 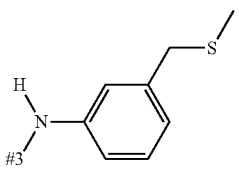 |
| W-267 | 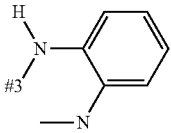 |
| W-269 | 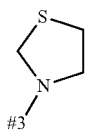 |
| W-270 | 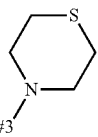 |
| W-271 | 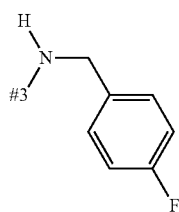 |

II. BIOLOGICAL EXAMPLES FOR FUNGICIDAL ACTIVITY

The fungicidal action of the compounds of formula I was demonstrated by the following experiments:

A. Glass House Trials

The spray solutions were prepared in several steps: The stock solution was prepared as follows: 0.84 mL of a 1:1 mixture of cyclohexanone and dimethylsulfoxide was added to 16.8 mg of active ingredient. Next, 27.2 mL of a mixture of water, acetone (10%), the emulsifier Wettol (0.1%) and the wetting agent Silwet (0.05%) was added. This stock solution was then further diluted with the described solvent-emulsifier-water mixture to the desired concentrations. After the final cultivation period the extent of fungal attack on the leaves was visually assessed as % diseased leaf area.

Use Example 1: Preventative Control of Brown Rust on Wheat Caused by *Puccinia recondita*

The first fully developed leaves of pot grown wheat were sprayed to run-off with an aqueous suspension, containing the desired concentration of active ingredient. The next day the treated plants were inoculated with spores of *Puccinia recondita* by shaking heavily infestated stock plants over the treated pots. After cultivation in the greenhouse for 7 days at 21-23° C. and a relative humidity between 40 to 70% the extent of fungal attack on the leaves was visually assessed as % diseased leaf area.

In this test, the plants which had been treated with 600 ppm of the active compound I-7, I-10, I-11, I-12, I-19, I-20, I-24, I-25, I-28, I-29, I-30, I-31, I-32, I-34, I-35, I-41, I-42, I-44, I-45, I-47, I-49, I-53, I-55, I-57, I-65, I-66, I-67, I-69, I-70, I-73, I-83, I-84, I-86, I-87, I-88, I-89, I-90, I-91, I-94, I-95, I-97, I-99, I-114, I-129, I-130, I-131, I-134, I-141, I-143, I-146, I-148, I-149, I-152, I-153, I-155, I-157, I-159, I-160, I-161, I-162, I-165, I-170, I-171, I-172, I-173, I-174, I-175, I-182, I-184, I-185, I-189, I-190, I-191, I-193, I-196, I-199, I-201, I-202, I-203, I-211, I-213, I-215, I-216, I-217, I-220, I-224, I-232, I-242, I-245, I-246, I-248, I-250, I-254, I-256, I-257, I-283, I-287 showed a diseased leaf area of at most 20%, whereas the untreated plants showed 80-100% diseased leaf area.

In this test, the plants which had been treated with 300 ppm of the active compound I-96, I-98, I-101, I-103, I-106, I-107, I-112, I-113, I-116, I-117, I-119, I-120, I-122, I-124, I-133, I-136, I-229, I-249 showed a diseased leaf area of at most 20%, whereas the untreated plants showed 80-100% diseased leaf area.

In this test, the plants which had been treated with 100 ppm of the active compound I-102, I-105, I-118, I-154, I-207, I-230, I-231, I-240, I-260, I-288 showed a diseased leaf area of at most 20%, whereas the untreated plants showed 80%-100% diseased leaf area.

In this test, the plants which had been treated with 79 ppm of the active compound I-235, I-245 showed a diseased leaf area of at most 20%, whereas the untreated plants showed 80%-100% diseased leaf area.

Use Example 2

Preventative control of powdery mildew caused by *Blumeria graminis* f. sp. *tritici*. The first fully developed leaves of pot grown wheat were sprayed to run-off with an aqueous suspension, containing the desired concentration of active ingredient. The next day the treated plants were inoculated with spores of *Blumeria graminis* f. sp. *tritici* (=syn. *Erysiphe graminis* f. sp. *tritia*) by shaking heavily infestated stock plants over the treated pots. After cultivation in the greenhouse for 7 days at 21-23° C. and a relative humidity between 40 to 70% the extent of fungal attack on the leaves was visually assessed as % diseased leaf area.

In this test, the plants which had been treated with 600 ppm of the active compound I-20, I-30, I-48, I-69, I-134 showed a diseased leaf area of at most 20%, whereas the untreated plants showed 80-100% diseased leaf area.

Use Example 3: Curative Action Against *Phakopsora pachyrhizi* on Soybeans (Rust of Soybean)

Leaves of pot-grown soy bean seedlings were inoculated with spores of *Phakopsora pachyrhizi*. To ensure the success of the artificial inoculation, the plants were transferred to a humid chamber with a relative humidity of about 95% and 20 to 24° C. for 24 h. The next day the plants were sprayed to run-off with an aqueous suspension, containing the desired concentration of active ingredient. The plants were allowed to air-dry. Then the trial plants were cultivated for 14 days in a greenhouse chamber at 23-27° C. and a relative humidity between 60 and 80%. The extent of fungal attack on the leaves was visually assessed as % diseased leaf area.

In this test, the plants which had been treated with 600 ppm of the active compound I-1, I-2, I-3, I-4, I-5, I-6, I-7, I-8, I-9, I-10, I-11, I-12, I-13, I-14, I-15, I-16, I-17, I-18, I-19, I-20, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-47, I-48, I-49, I-50, I-51, I-52, I-53, I-54, I-55, I-56, I-57, I-58, I-59, I-60, I-61, I-62, I-63, I-64, I-65, I-66, I-67, I-68, I-69, I-70, I-71, I-72, I-73, I-79, I-82, I-83, I-84, I-85, I-86, I-87, I-88, I-89, I-90, I-91, I-92, I-94, I-95, I-99, I-108, I-126, I-128, I-132, I-134, I-135, I-137, I-140, I-141, I-143, I-150, I-173, I-184, I-218, I-224, I-244, I-246, I-247, I-263 showed a diseased leaf area of at most 20%, whereas the untreated plants showed 80-100% diseased leaf area.

In this test, the plants which had been treated with 300 ppm of the active compound I-96, I-97, I-98, I-100, I-101, I-103, I-106, I-107, I-109, I-110, I-111, I-112, I-113, I-114, I-116. I-117, I-118, I-119, I-120, I-122, I-124, I-129, I-130, I-131, I-133, I-136, I-148, I-149, I-152, I-155, I-157, I-160, I-161, I-171, I-172, I-174, I-175, I-182, I-189, I-191, I-199, I-205, I-217, I-220, I-229, I-242, I-246, I-248, I-249, I-250, I-256, I-283 showed a diseased leaf area of at most 20%, whereas the untreated plants showed 80-100% diseased leaf area.

In this test, the plants which had been treated with 100 ppm of the active compound I-102, I-105, I-115, I-144, I-145, I-146, I-147, I-154, I-156, I-158, I-159, I-162, I-163, I-165, I-168, I-169, I-170, I-176, I-178, I-180, I-183, I-185, I-186, I-187, I-192, I-193, I-194, I-196, I-198, I-200, I-201, I-203, I-207, I-208, I-210, I-211, I-212, I-213, I-214, I-215, I-216 I-219, I-222, I-223, I-225, I-226, I-230, I-231, I-232, I-233, I-237, I-238, I-240, I-254, I-255, I-257, I-259, I-260, I-261, I-277, I-284, I-286, I-287, I-288 showed a diseased leaf area of at most 20%, whereas the untreated plants showed 80-100% diseased leaf area.

In this test, the plants which had been treated with 79 ppm of the active compound I-149, I-153, I-236, I-245 showed a diseased leaf area of at most 20%, whereas the untreated plants showed 80-100% diseased leaf area.

In this test, the plants which had been treated with 75 ppm of the active compound I-236, I-241 showed a diseased leaf area of at most 20%, whereas the untreated plants showed 80-100% diseased leaf area.

Use Example 4: Preventative Control of Leaf Blotch on Wheat Caused by Septoria tritici Leaves of pot-grown wheat seedling were sprayed to run-off with an aqueous suspension of the active compound, prepared as described. The plants were allowed to air-dry. At the following day the plants were inoculated with an aqueous spore suspension of Septoria tritici. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area.

In this test, the plants which had been treated with 600 ppm of the active compound I-20, I-42, I-47, I-69, I-140, I-170, I-288 showed a diseased leaf area of at most 20%, whereas the untreated plants showed 80-100% diseased leaf area.

In this test, the plants which had been treated with 300 ppm of the active compound I-129, I-130, I-152, I-157, I-174 showed a diseased leaf area of at most 20%, whereas the untreated plants showed 80-100% diseased leaf area.

In this test, the plants which had been treated with 100 ppm of the active compound I-154, I-159, I-162, I-163, I-176, I-207 showed a diseased leaf area of at most 20%, whereas the untreated plants showed 80-100% diseased leaf area.

The invention claimed is:
1. An agrochemical composition comprising an auxiliary and a compound of formula I

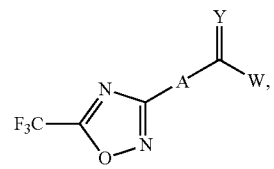

wherein:
A is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^A$; wherein
  $R^A$ is halogen, cyano, $NO_2$, OH, SH, $NH_2$, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and alicyclic moieties are unsubstituted or substituted by 1, 2, 3 or 4 identical or different groups $R^a$; wherein
  $R^a$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl, $C_1$-$C_4$-alkoxy-$C_1$-$C_4$-alkyl;
Y is O or S;
W is $NR^1R^2$; wherein
  $R^1$, $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)—($C_1$-$C_6$-alkyl), C(=O)—($C_1$-$C_6$-alkoxy), phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$; or $R^1$ and $R^2$ together with the nitrogen atom to which they are bound form a saturated or partially unsaturated mono- or bicyclic 3- to 10-membered heterocycle, wherein the heterocycle includes beside one nitrogen atom and one or more carbon atoms 1, 2 or 3 heteroatoms independently selected from N, O and S as ring member atoms; and wherein one or two $CH_2$ groups of the heterocycle may be replaced by one or two groups independently selected from the group of C(=O) and C(=S); and wherein the heterocycle is unsubstituted or carries 1, 2, 3, 4 or up to the maximum possible number of identical or different groups $R^{1a}$; wherein $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $NHSO_2$-$C_1$-$C_4$-alkyl, —(C=O)$C_1$-$C_4$-alkyl, C(=O)—$C_1$-$C_4$-alkoxy, $C_1$-$C_6$-alkylsulfonyl, hydroxy$C_1$-$C_4$-alkyl, C(=O)—$NH_2$, C(=O)—$NH(C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl or $C_1$-$C_4$-alkoxy-$C_1$-$C_4$-alkyl;

or an N-oxide or an agriculturally acceptable salt thereof.

2. The composition of claim 1, wherein A is phenyl.

3. The composition of claim 1, wherein Y is O.

4. The composition of claim 1, wherein $R^1$ is hydrogen, $C_1$-$C_6$-alkyl, $C_2$-$C_6$-alkenyl or $C_2$-$C_6$-alkynyl and $R^2$ is phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle, wherein the ring includes besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$.

5. The composition of claim 4, wherein W is $NR^1R^2$ and wherein $R^1$ and $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl; and wherein the alicyclic and the cyclic groups are unsubstituted or substituted by 1, 2, 3 or up to the maximum possible number of identical or different groups $R^{1a}$.

6. The agrochemical composition according to claim 1 further comprising at least one further pesticidally active substance.

7. The agrochemical composition according to claim 1 further comprising seed, wherein the amount of the compound of the formula I, or an N-oxide, or an agriculturally acceptable salt thereof, is from 0.1 g to 10 kg per 100 kg of seed.

8. A method for combating phytopathogenic harmful fungi comprising treating fungi or materials, plants, soil or seeds to be protected against fungal attack, with an effective amount of the composition of claim 1.

9. The method of claim 8, wherein A is phenyl.

10. The method of claim 8, wherein Y is O.

11. The method of claim 8, wherein $R^1$ is hydrogen, $C_1$-$C_6$-alkyl, $C_2$-$C_6$-alkenyl or $C_2$-$C_6$-alkynyl and $R^2$ is phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle, wherein the ring includes besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$.

12. The method of claim 8, wherein $R^1$ and $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl; and wherein the alicyclic and the cyclic groups are unsubstituted or substituted by 1, 2, 3 or up to the maximum possible number of identical or different groups $R^{1a}$.

13. The composition of claim 1, wherein $R^1$ is hydrogen and $R^2$ is phenyl; and wherein the phenyl group is unsubstituted or substituted by 1, 2, 3, 4 or up to the maximum possible number of identical or different groups $R^{1a}$; and wherein $R^{1a}$ is halogen, cyano, $C_1$-$C_6$-alkyl, $C_1$-$C_6$-haloalkyl, $C_1$-$C_6$-alkoxy, $C_1$-$C_6$-haloalkoxy or $C_3$-$C_8$-cycloalkyl.

14. The composition of claim 1, wherein $R^1$ is hydrogen and $R^2$ heteroaryl-$C_1$-$C_4$-alkyl; and wherein any of the aliphatic or cyclic groups are unsubstituted or substituted by 1, 2, 3 or up to the maximum possible number of identical or different groups R1a; and wherein R1a is halogen, cyano, $C_1$-$C_6$-alkyl, $C_1$-$C_6$-haloalkyl, $C_1$-$C_6$-alkoxy, $C_1$-$C_6$-haloalkoxy or $C_3$-$C_8$-cycloalkyl.

15. The method of claim 8, $R^1$ is hydrogen and $R^2$ is phenyl; and wherein the phenyl group is unsubstituted or substituted by 1, 2, 3, 4 or up to the maximum possible number of identical or different groups $R^{1a}$; and wherein $R^{1a}$ is halogen, cyano, $C_1$-$C_6$-alkyl, $C_1$-$C_6$-haloalkyl, $C_1$-$C_6$-alkoxy, $C_1$-$C_6$-haloalkoxy or $C_3$-$C_8$-cycloalkyl.

16. The method of claim 8, wherein $R^1$ is hydrogen and $R^2$ heteroaryl-$C_1$-$C_4$-alkyl; and wherein any of the aliphatic or cyclic groups are unsubstituted or substituted by 1, 2, 3 or up to the maximum possible number of identical or different groups R1a; and wherein R1a is halogen, cyano, $C_1$-$C_6$-alkyl, $C_1$-$C_6$-haloalkyl, $C_1$-$C_6$-alkoxy, $C_1$-$C_6$-haloalkoxy or $C_3$-$C_8$-cycloalkyl.

* * * * *